(12) United States Patent
Gilbert et al.

(10) Patent No.: US 6,774,116 B2
(45) Date of Patent: Aug. 10, 2004

(54) PRODRUGS VIA ACYLATION WITH CINNAMATE

(75) Inventors: Carl W. Gilbert, Powder Springs, GA (US); Eleanor B. McGowan, Smyrna, GA (US); Kirby S. Black, Acworth, GA (US); T. Gregory P. Harper, Stockton, CA (US)

(73) Assignee: Cryolife, Inc., Kennesaw, GA (US)

( * ) Notice: Subject to any disclaimer, the term of this patent is extended or adjusted under 35 U.S.C. 154(b) by 226 days.

(21) Appl. No.: 10/066,306

(22) Filed: Jan. 31, 2002

(65) Prior Publication Data

US 2002/0187992 A1 Dec. 12, 2002

Related U.S. Application Data

(60) Provisional application No. 60/284,304, filed on Apr. 17, 2001, and provisional application No. 60/315,782, filed on Aug. 28, 2001.

(51) Int. Cl.[7] .................... A61K 31/704; A61K 31/495; C07C 57/44
(52) U.S. Cl. .................. 514/34; 514/396; 514/529; 514/252.12; 514/785; 514/568; 514/554; 514/614; 514/613; 564/164; 564/167; 560/45; 548/542; 544/358
(58) Field of Search .................. 514/34, 396, 529, 514/252.12, 785, 568, 554, 614, 613; 564/164, 167; 560/45, 104, 1; 548/542; 544/358; 546/341; 549/499; 526/318.1

(56) References Cited

U.S. PATENT DOCUMENTS 5,114,851 A * 5/1992 Porter et al.

OTHER PUBLICATIONS

Li et al. (Guangdong Yixue (1997), 18 (5), 345) (abstract sent).*

* cited by examiner

Primary Examiner—Samuel Barts
Assistant Examiner—Michael C. Henry
(74) Attorney, Agent, or Firm—Muserlian, Lucas & Mercanti, LLP

(57) ABSTRACT

A prodrug composition containing a cinnamate moiety and a biologically active molecule moiety which can be released by hydrolysis or activated by light is disclosed. The cinnamate moiety can have substituents of various electronically donating or electronically withdrawing groups to modify the cinnamate moiety's electric properties as well as photo reactivities for the purpose of achieving a proper hydrolysis rate of the acyl bond between the biologically active molecule moiety and the cinnamic acid backbone. The biologically active molecule can be any biologically active agent or diagnostic, for example, a chemotherapeutic such as a paclitaxel, campotothecin, doxorubicin, amethopterin, etoposide, or fluconazole. The prodrug composition can be modified to add a carrier moiety on the prodrug composition for targeting or to facilitate uptake of the drug. The prodrug compositions can be activated with an energy source to release the drug at the desired site. Representative energy sources can be in the form of electric force, ultrasound, light or radiation of a radioactive material which can be administered either externally or internally.

34 Claims, 10 Drawing Sheets

PRODRUGS VIA ACYLATION WITH CINNAMATE

CROSS REFERENCE TO RELATED APPLICATIONS

Figure 1:
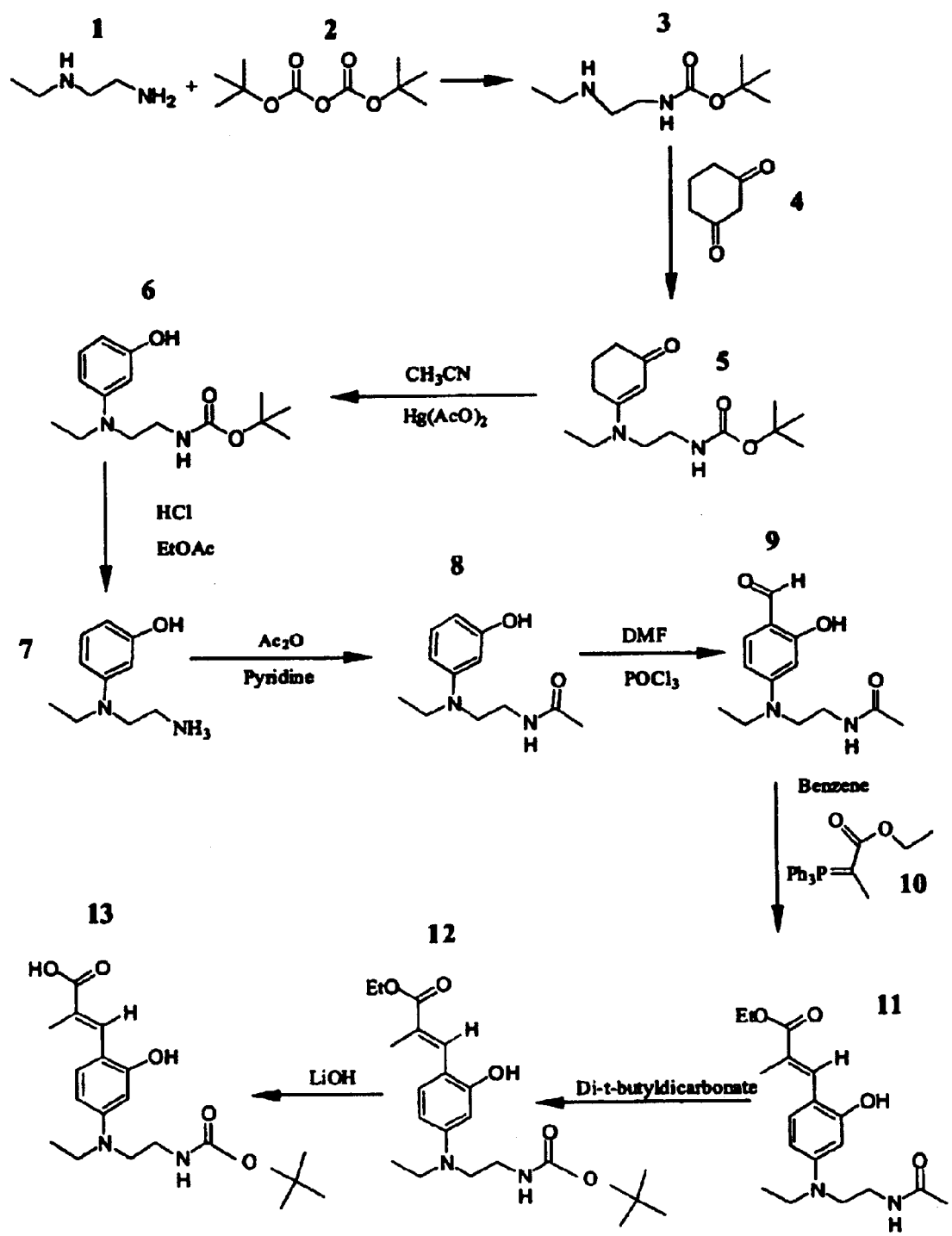

This application claims the benefit of priority from U.S. Provisional Patent Application Serial No. 60/284,304 filed Apr. 17, 2001 and U.S. Provisional Patent Application Serial No. 60/315,782 filed Aug. 28, 2001 the contents of each of which are incorporated herein by reference.

BACKGROUND OF THE INVENTION

The present application relates generally to energy-reversible compositions containing drugs or other molecules. In particular, the present application relates to drug moieties and other biologically active moieties, herein denoted —$X_1A$, bonded to a cinnamic acid or related molecular core (herein denoted Z—CINN).

In prodrugs, an active drug is typically bonded to another molecule to alter the drug's properties in a reversible manner and regulate the drug's release. The majority of prodrugs have an ester or amide bond formed between a hydroxyl, amino, or thiol group of a drug moiety and the carboxylate group of a carrier molecule, or vice versa. Depending on the chemical properties of the molecules making up the linkage, these prodrugs have hydrolysis rates that range from minutes to days. Temperature, pH and the chemical composition of the solution in which the prodrug is administered can also influence the rate of release of the active ingredient from the prodrug. The very short hydrolysis rates and very long ones are generally not useful. Hydrolysis rates in the range of 0.5–48 hours are generally more desirable. Prodrugs can be designed 1) to change aqueous solubility properties of the drug, 2) to change circulating lifetime of the drug, 3) to be more lipophilic than the parent compound, allowing greater penetration of biological membranes and therefore greater access to diseased sites, 4) to have lower toxicity, for example, by allowing the prodrug to be transported to its site of action in its inactive form, where the inactive prodrug is converted to the active parent compound at its target site, 5) to bind selectively at a target site, because of a specific targeting molecule attached to the prodrug complex, or for other purposes.

Over the years, a large number of prodrugs have been developed. For example, some have suggested preparing amino acid esters of various therapeutic agents. Others have suggested forming polymeric conjugates with ester linkages. In either case, the active compound is released in vivo via hydrolysis. Another approach is described in U.S. Pat. No. 6,071,908 which discloses a method of treating neoplastic disease using a radiation-activated cytotoxin prodrug. The prodrug releases a tumoricidal cytotoxic effector using reducing agents generated by the radiolysis of water.

A still further prodrug approach relies upon the use of light for reversible control of enzyme activity, (see U.S. Pat. Nos. 5,114,851 and 5,218,137 to Porter et al.). Specifically, Porter et al. disclose coupling an enzyme active site amino acid residue to cinnamate (CINN) derivatives to form o-hydroxy cinnamate substituted esters or acyl enzymes, which are inactive. On photolysis, the bond with the active site amino acid residue is cleaved and the active site is exposed. There are a number of potential advantages associated with this concept. In theory, using this technique, the artisan has the ability to control in vivo enzyme activity specifically and rapidly, by exposure to light in vivo or ex vivo.

In spite of the advances of Porter et al., work in this area has continued. There continues to be a need in the art to expand the cinnamate core platform beyond inhibited enzymes. It would also be desirable to provide a means for better targeting non-enzyme therapeutic compounds to sites of interest in the body. In the past, the artisan has had little ability to control when and in what amount a drug can be generated in the therapeutically desired area. Moreover, the ability to reduce the amount of administered drug and/or peripheral organ damage caused by untargeted delivery would be welcomed by those in the art. It would also be advantageous to have the capability to independently initiate or control the hydrolysis of a prodrug. It would also be advantageous to have a means to localize a prodrug or other conjugate to a diseased area. The present invention addresses these and other needs.

SUMMARY OF THE INVENTION

It is an object of the present invention to provide improved compositions designated herein as Z—CINN—$X_1$—A, that can controllably release the —$X_1A$ portion thereof at a controlled rate, whether by hydrolysis or by energy input such as light or ultrasound.

It is another object of the present invention to provide means to facilitate the targeting, delivery and binding of a composition containing Z—CINN—$X_1A$ to a surface or a diseased site, by incorporation of additional molecule(s) attached to Z—CINN, denoted B-L, which are capable of binding to that site, to concentrate the conjugate prior to release of —$X_1A$.

It is another object of the present invention to provide an additional site on Z—CINN—$X_1$—A compounds which can be derivatized in various ways, including with groups designated herein as "B-L", to provide compositions designated herein as B-L-Z—CINN—$X_1$—A, which have additional properties, such as stability, increased circulation time, targeting capacity, or immobilization to appropriate supports.

It is therefore an object of the present invention to provide a prodrug composition, and the method of preparation thereof, which releases an effective drug at a controlled rate by application of an exogenous stimulus.

It is another object of the present invention to provide means to facilitate the delivery of a prodrug composition to a diseased site by incorporation of a targeting molecule.

It is another object of the present invention to provide means to alter a prodrug composition by incorporation of a molecule(s) to increase circulation time, solubility, or stability.

It is another object of the present invention to provide means to alter a prodrug composition by incorporation of a molecule(s) which can bind to a biological or non-biological surface such as a bead, stent, or other matrix material for purposes of slow release, purification of additional molecules, and the like.

It is another object of the present invention to bind and release biologically active molecules, other than enzymes, in the manner specified above.

These and other objects are provided by the present invention, which in one embodiment provides compounds corresponding to Z—CINN—$X_1$—A and the formula:

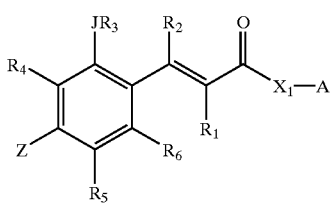

Formula I wherein:

$X_1A$ is a residue of a releasable biologically active moiety;

$R_1$ and $R_2$ are individually selected from the group consisting of H, $CH_3$, $C_2$–$C_{10}$ alkyls, $C_2$–$C_{10}$ alkenyls or $C_2$–$C_{10}$ alkynyls, each of which can be substituted or unsubstituted; straight or branched, $C_2$–$C_{10}$ heteroalkyls, $C_2$–$C_{10}$ heteroalkenyls or $C_2$–$C_{10}$ heteroalkynyls and —$(CR_{15}R_{16})_p$—D;

wherein: $R_{15}$ and $R_{16}$ are individually selected from the group consisting of H, $CH_3$, $C_2$–$C_{10}$ alkyls, $C_2$–$C_{10}$ alkenyls or $C_2$–$C_{10}$ alkynyls, each of which can be substituted or unsubstituted; straight or branched; and $C_2$–$C_{10}$ heteroalkyls, $C_2$–$C_{10}$ heteroalkenyls or $C_2$–$C_{10}$ heteroalkynyls;

p is a positive integer from 1 to about 12;

D is selected from among —SH, —OH, $X_2$, —CN, —$OR_{19}$, $NHR_{20}$,

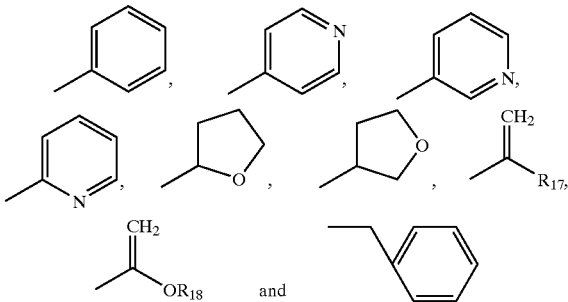

wherein:

$R_{17}$ is H, $CH_3$ or $X_3$;

$R_{18}$ is H, a $C_1$–$C_4$ alkyl or benzyl;

$R_{19}$ is H, a $C_{1-4}$ alkyl, $X_2$ or benzyl;

$R_{20}$ is H, $C_{1-10}$ alkyls or —$C(O)R_{21}$, wherein $R_{21}$ is H, a $C_{1-4}$ alkyl or alkoxy, t-butoxy or benzyloxy;

$X_2$ and $X_3$ are independently selected halogens;

$R_3$ is H, $CH_3$, or —$C(=O)(CR_{15}R_{16})_w$—D, where w is 0 or an integer from 1 to about 12, and D is H or as described for $R_1$ and $R_2$ J is O, NH or S;

$R_4$, $R_5$, and $R_6$ are independently selected from the group consisting of H, $CH_3$, $C_2$–$C_{10}$ alkyls, $C_2$–$C_{10}$ alkenyls or $C_2$–$C_{10}$ alkynyls, each of which can be substituted or unsubstituted; straight or branched; $C_2$–$C_{10}$ heteroalkyls, heteroalkenyls or heteroalkynyls and halogens;

Z is H, $NR_7R_8$ or

wherein $R_7$ is selected from among H, $CH_3$, $C_2$–$C_{10}$ alkyls, alkenyls or alkynyls which can be substituted or unsubstituted; straight or branched; $C_2$–$C_{10}$ heteroalkyls, heteroalkenyls or heteroalkynyls, or —$(CR_{23}R_{24})_q$—aryl, or $R_8$, wherein $R_{23}$ and $R_{24}$ are independently selected from the group consisting of H and $C_1$–$C_{10}$ alkyls;

q is an integer from 1 to about 6;

$R_8$ is selected from the group consisting of $(CR_9R_{10})_n$—$NR_{22}$—$R_{11}$, $(CR_9R_{10})_n$—$CH_2$—$NHC(O)R_{26}$ and $(CR_9R_{10})_n$—$CH_2$—E;

wherein $R_9$ and $R_{10}$ are independently selected from the group consisting of H, $CH_3$, $C_2$–$C_{10}$ alkyls, $C_2$–$C_{10}$ alkenyls or $C_2$–$C_{10}$ alkynyls, each of which can be substituted or unsubstituted; straight or branched; $C_2$–$C_{10}$ heteroalkyls, $C_2$–$C_{10}$ heteroalkenyls or $C_2$–$C_{10}$ heteroalkynyls and halogens;

$R_{26}$ is H, $CH_3$, O-t-butyl, O-benzyl;

E is OH, SH or O—$C(O)R_{27}$, wherein $R_{27}$ is a $C_1$–$C_6$ alkyl, benzyl or phenyl;

$R_{22}$ is H or $CH_3$;

n is a positive integer from 1 to about 10;

$R_{11}$ is H or -L-B, wherein L is a linker; and

B is a second active moiety, reactive group moiety or a polymer; and $R_{25}$ is H, —$C(O)$—$R_{28}$ or —$C(O)$—$O$—$R_{29}$, wherein $R_{28}$ is a $C_1$–$C_6$ alkyl or benzyl; and $R_{29}$ is $CH_3$, t-butyl or benzyl.

Pharmaceutically acceptable salts, including $Cl^-$, $Br^-$, $HSO_4^-$, etc., are also provided.

In some preferred aspects, $X_1A$ is a residue of a biologically active molecule such as paclitaxel or another chemotherapeutic agent (drug) which bonds to Z—CINN as a prodrug.

In still further aspects of the invention, Z—CINN—$X_1A$ compositions are derivatized utilizing the reactive Z site of Formula I. In particular, when $R_8$ is $(CR_9R_{10})$—$NR_{22}$—$R_{11}$, and $R_{11}$ is L-B, the artisan is provided with light activatable prodrugs which are linked to, among other things, targeting antibodies or polymers such as PEG or other polymers. The moiety "B" can be —H, or a natural polymer, such as DNA, a synthetic polymer, such as PEG, synthetic or naturally occurring organic molecule, or natural or synthetic targeting peptide, polypeptide or protein such as a monoclonal antibody (mAb).

In other aspects of the invention, H—$X_1A$ is a biologically active molecule or moiety such as a protein whose side-chain —O, —S or —NH corresponds to $X_1$ of Formula (I) which is bonded to the C(=O) of the Z—CINN. Thus, H—$X_1A$ is a drug, etc. rendered inactive through its bond to Z—CINN and is preferably capable of having its biological activity restored by one or more of hydrolysis, exposure to light or other energy source after targeting has been allowed to proceed in vivo.

As a result of the present invention, several advantages are provided. For example, these Z—CINN—$X_1$—A inactivated compositions can have various beneficial properties, such as increased targeting ability, solubility, increased half-life in circulation, or other features. In addition, L-Z—CINN—$X_1$—A inactivated compositions can be immobilized by crosslinking to support materials via the linker L. The support materials can be any industrially or pharmaceutically suitable materials such as organic polymers, inorganic polymers, natural polymers, biopolymers or zeolites and can be in the form of films, membranes, filters, beads, particles, resins, microparticles, or columns. Alternatively, B-L-Z—CINN—$X_1$—A can be attached to supports by mechanisms such as affinity or by additional coupling reactions with activated support materials.

The composition of Formula I, B-L-Z—CINN-$X_1$A, can be used with a pharmaceutically acceptable carrier for administration to a patient. In one embodiment, the carrier is one of liposomes, microcapsules, enteric coated formulations, and formulations for pulmonary (inhalation) administration.

The acyl bond connecting Z—CINN and —$X_1$A is susceptible to hydrolysis and/or energy activation. Absent energy activation, the acyl bond can be relatively stable at a approximately neutral pH is the dark. Upon energy activation, the acyl bond is rapidly hydrolyzed to release biologically active H$X_1$A. In one embodiment, H$X_1$A is released following exposure to a source of radiation such as visible light, infrared light, ultraviolet light, ultrasound, microwave, and radiation. In anther embodiment, the energy source is radiation generated by a radioactive material such as U*, Co*, Fe*, I*, Cs* or Tc* (M* denotes a radioactive material). In a preferred embodiment, the energy source is light with a wavelength in the range from 300 to 850 nm. In one specifically preferred embodiment, the light has a wavelength in the range from 300 nm to 450 nm. The most preferred light has a wavelength in the range from 350 nm to 420 nm.

In further aspects of the invention, methods of preparing and using the compositions of the present invention are also provided.

BRIEF DESCRIPTION OF THE DRAWINGS

FIG. 1 illustrates the synthesis of (3-[2-hydroxy4-(ethyl)(2-tert-butyloxycarbamidoethyl)amino]phenyl-2-methyl-2-propenoic acid, ethyl ester).

FIG. 2 illustrates general synthetic schemes for the synthesis of various Z—CINN—$X_1$A compounds of the present invention.

FIGS. 3–6 provide reaction schemes corresponding to Examples 1–5.

FIGS. 7–10 provide in vivo data corresponding to Example 6.

DETAILED DESCRIPTION OF THE INVENTION

I. Definitions

The term "reactivation" as used herein refers to the process in which the prodrug is transformed to regenerate the parent compound H—$X_1$A, such as by cleavage of the covalent acyl bond, for example by a source of energy.

The term "cinnamic acid" is the common or trivial name for 3-phenyl-2-propenoic acid. Z—CINN—$X_1$—A molecules include derivatives of cinnamic acid.

IUPAC names are given for synthesized compounds.

For purposes of the present invention, the terms "alkyl", "alkenyl" and "alkynyl" shall be understood to include, e.g., straight, branched, substituted, cyclo-derivatives thereof, including alkoxy or substituted cycloalkyls, etc. "Substituted" shall be understood to include halo-, alkoxy-, nitro-, etc.

For purposes of the present invention, "molecule" and "biologically active molecule" shall be understood to embrace not only organic or small molecules but also proteins, peptides and the like.

For purposes of the present invention, "halogen" shall be understood to include chlorine, fluorine, bromine, etc.

For purposes of the present invention, "—$X_1$A moiety" ("—$X_1$A") shall be understood to mean a residue or component of the B-L-Z—CINN—$X_1$A compound which regenerates the native or parent compound, H—$X_1$A, when the acyl bond of the Z—CINN is hydrolyzed.

For purposes of the present invention, "B-L moiety" ("B-L") shall be understood to mean a substituent on the Z—CINN—$X_1$A composition derived from a molecule or molecules which facilitate(s) the stability, delivery, or localization of B-L-Z—CINN—$X_1$A, for example, delivery to a disease site or a particular organ or region of the body.

For purposes of the present invention "reactive group", particularly as used to describe the variable B shall be understood to include those moieties capable of facilitating conjugation of L and one or more biologically active moieties or polymers, including but not limited to the free electron pair (double bond) of a maleimidyl residue.

For purposes of the present invention, "energy source" shall be understood to mean a form of energy. Energy sources are applied outside the patient's body or administered within the patient, for example, using afiber-optic catheter, ultrasonic tipped catheter or radiation implant.

II. Prodrugs With Cinnamic Acid Backbone

Hydrolysis of an acyl (ester or amide) bond is a function of the stability of the whole molecule. The cinnamic acid backbone (Z—CINN) is subject to compositional or structural modification. One or more substituents that modify the chemical properties of the cinnamic acid backbone can be introduced, thus allowing an effective modulation of the hydrolysis rate of the acyl bond formed between Z—CINN and the —$X_1$A moiety, as well as the photoactivity of Z—CINN—$X_1$A.

Z—CINN compound is selected based on the desired hydrolysis rate of the acyl bond and desired photoactivity of Z—CINN—$X_1$A. Hydrolysis rate of the acyl bond depends on the steric and electronic properties of this composition. Generally speaking, an electronically withdrawing group will decrease the electronic density of Z—CINN, therefore increasing the tendency of a water molecule to attack the carbonyl group and thus increasing the hydrolysis rate of the acyl bond. An electronically donating group, on the other hand, will increase the electronic density of Z—CINN, therefore decreasing the tendency of a water molecule to attack the carbonyl group and thus decreasing the hydrolysis rate of the acyl bond. Similarly, a sterically hindering group or substituent will tend to block the attack of a water molecule on the carbonyl group of the acyl bond, therefore decreasing the hydrolysis rate of the acyl bond.

The photoactivity of the prodrug largely depends on the electronic properties of Z—CINN. Generally speaking, an increase of the electronic density of a π-stacking system will render it susceptible to activation by light having higher wavelength while a decrease of the electronic density of a π stacking system will render it susceptible to activation by light having lower wavelength. In addition, an increase of the π-stacking system tends to shift the activation energy to light with longer wavelength while a decrease of the π-stacking system tends to shift the activation energy to light with shorter wavelength. Substituents with various electronic properties can be used to modify the photoactivity of the cinnamic acid backbone. The substituents can be any electronically withdrawing groups or electronically donating groups such as those listed in Formula I. One skilled in the art will be able to determine, on the basis of the desired light or energy source and the desired hydrolysis rate range, to select a Z—CINN backbone needed to generate a Z—CINN—$X_1$A composition.

III. Z—CINN Derivatives

A. Z—CINN

Various compositions can be formed using Z—CINN as a core molecule. A variety of functional groups can be introduced into Z—CINN to modify its chemical as well as physical properties. These compositions can also have different reactivities toward a nucleophile or light. Some preferred compounds are discussed in detail below.

The Z—CINN core molecule has the formula

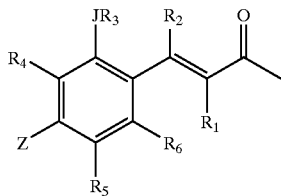

Formula (II)

wherein all variables are as set forth in Formula (I) above.

In one preferred embodiment for Formulas (I) and (II), Z is $NR_7R_8$. Further, $R_1, R_2, R_3, R_4, R_5$, and $R_6$ are H or lower alkyl groups such as $CH_3$ or $CH_2CH_3$. In another preferred embodiment for Formulas (I) and (II), $R_7$ is $CH_3CH_2$ and $R_8$ is —$(CR_9R_{10})_n$—$NR_{22}$—$R_{11}$ and $R_9$ and $R_{10}$ are H; wherein n is 2; and $X_1$ is O, S or NH. In those aspects of the invention where J is O and Z is $NR_7R_8$, some preferred $R_8$ groups include:

1. $(CH_2)_n$—$NH_2$ and salts thereof, e.g. —$NH_3^+$:$Cl^-$ or $Br^-$ or $HSO_4^-$, etc.
2. $(CH_2)_n$—NH—C(=O)—H
3. $(CH_2)_n$—NH—C(=O)—$CH_3$
4. $(CH_2)_n$—NH—C(=O)—O-t-butyl
5. $(CH_2)_n$—NH—C(=O)—O— benzyl
6. $(CH_2)_n$—OH
7. $(CH_2)_n$—SH
8. $(CH_2)_n$—O—C(=O)—$R_{21}$; wherein $R_{21}$ is $CH_3$, $C_{1-6}$ alkyl or phenyl;

wherein each of the above n is an integer of from 2 to about 10, preferably 2–4.

In still a further aspect of the invention, Z is substituted piperazine thereby providing compositions of the Formula (Ia):

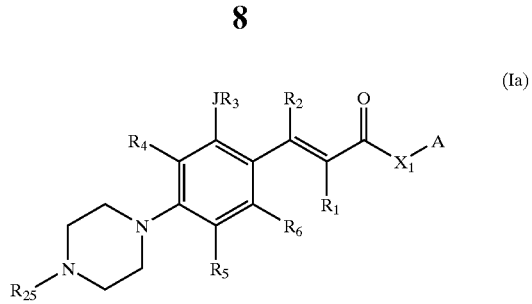

(Ia)

wherein all the variables are as previously defined, with regard to Formula (I).

Generally, the cinnamic acid backbone can be synthesized using standard techniques and available reagents by those skilled in the art. The cinnamic acid backbone then serves as the primary reactant with the parent compound described herein as H—$X_1$A to form the prodrug.

Referring now to FIG. 1 by way of example, synthesis of a cinnamic acid backbone is illustrated. Specifically, an amine such as 2-ethylaminoethylamine (1) can react with an anhydride (2) to generate the amide (3). 3 condenses with 1,3-cyclohexanedione (4) followed by dehydration to generate 3-amino-2-cyclohexen-1-one (5). Dehydrogenation of 5 in the presence of a catalyst generates a 3-hydroxyphenyl amine (6). Hydrolysis removes a blocking group to obtain 7, followed by N-acylation to obtain 8. Reaction of 8 with $POCl_3$/DMF generates an aldehyde (9). Reaction of 9 with an appropriate Wittig reagent, carbethoxyethylidene triphenylphosphorane (10), generates 11, where the aldehyde group is converted to a 2-propenoic acid ethyl ester. The N-acyl group is exchanged to obtain 12, which is hydrolyzed in LiOH to obtain 13 (tBOC-N—CINN). The compounds of Formula (Ia) can be similarly prepared using piperazine in place of the amine (1). As will be appreciated by the artisan of ordinary skill, other groups can be substituted for alcohols in order to afford the artisan with the ability to link the cinnamic acid backbone to any number of alternative functional groups. Such alternatives are represented by Formula (III)

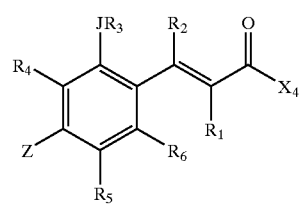

(III)

where all variables are as previously described in Formula (I) and $X_4$ is a reactive terminal group such as OH, NH. SH, halogen, e.g., fluorine, chlorine, bromine, iodine, or other reactive groups known in the art, including, without limitation, aldehydes, hydrazines, carbazates, tosyl, mesyl, paranitrophenyl, N-hydroxysuccinimidyl, maleimidyl, etc. and optionally includes a bifunctional spacer between Z—CINN and the terminal reactive group. Within this aspect of the invention, some particularly preferred compounds include:

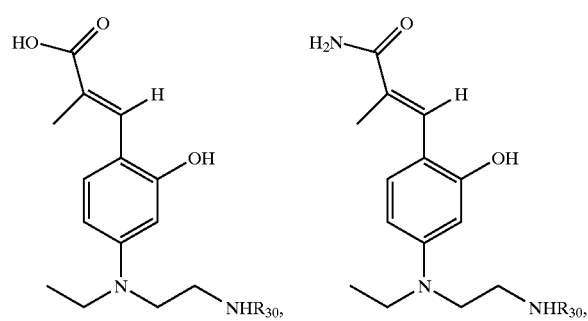
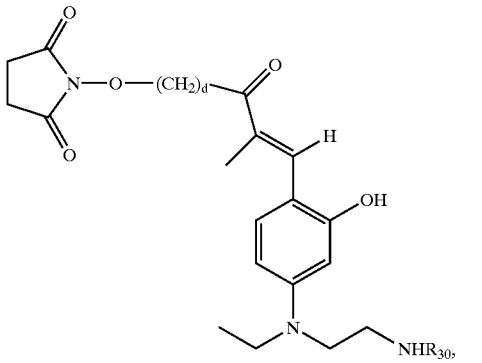
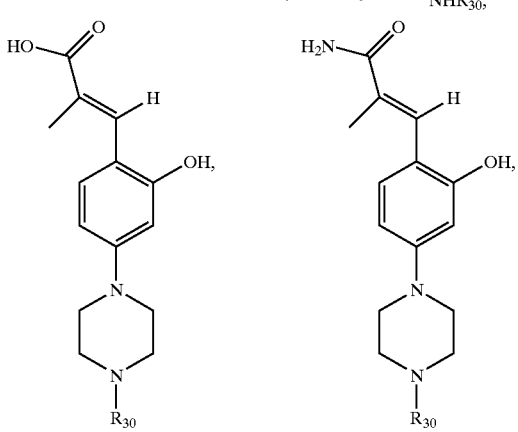
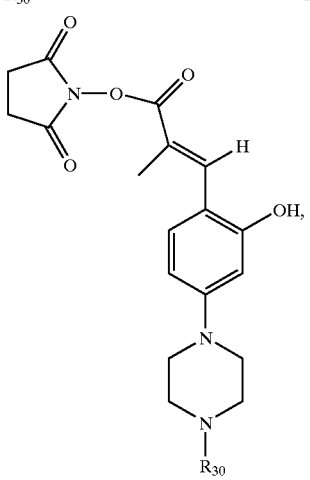
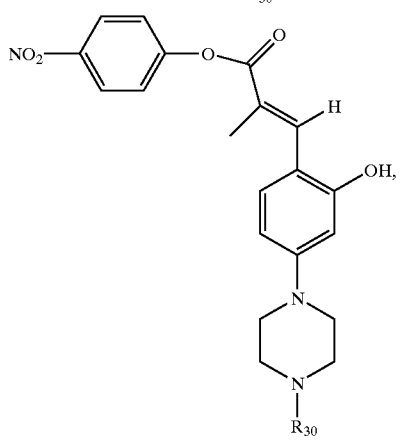

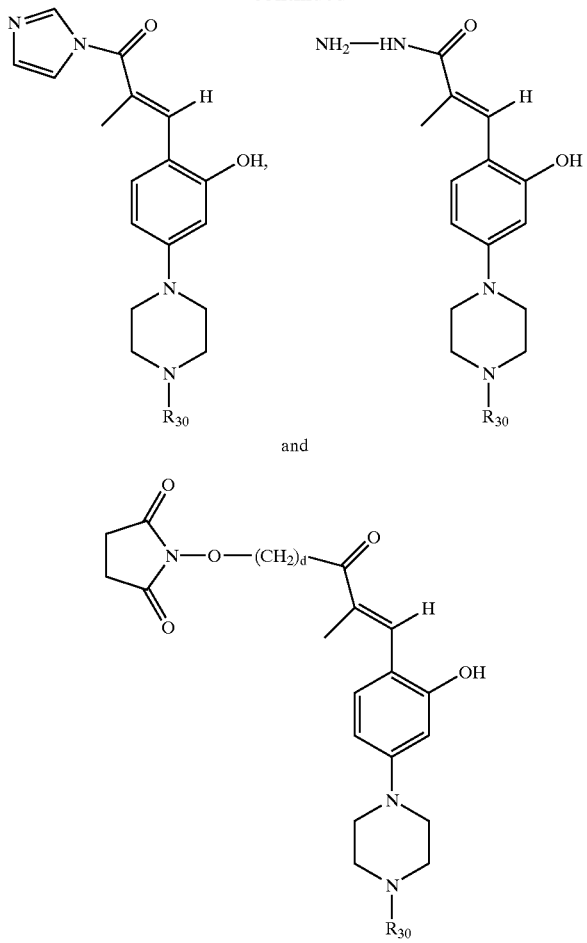

where $R_{30}$ is —H, -tBOC, fMOC, or a blocking group.

Using the above Formula (III) compounds as starting materials, prodrugs of various biologically active moieties are made using available amines, hydroxyls, carboxylic acids, thiols, etc on the parent compounds. See FIG. 2. Further examples include an amino acid derivative or peptide derivative being coupled to the N—CINN backbone (13) using standard coupling agents such as DCI/DMAP. Carboxyl groups on a peptide or amino acid would be protected with acceptable blocking groups prior to reaction. The amino group would then react with 13, DCI, and DMAP to give an amide bond, and the blocking groups would be removed. Similar procedures would be followed for alcohols or thiols.

As stated above, the parent compound of interest, e.g. H—$X_1$A, used to form Z—CINN—$X_1$A must have an available reactive group such as a hydroxyl group, a sulfhydryl group, or amine group. Suitable compounds include, without limitation, chemotherapeutics, antibiotics, antivirals, antifungals, or diagnostics, or the combination thereof, or any other molecules having other known functions, such as nucleic acids or fragments thereof, sugars, proteins, hormones, or peptides which can be linked to Z—CINN. Those skilled in the art will be able to add other molecules to this list. The parent molecule used to form the prodrug can be a protein, polysaccharide, nucleic acid molecule or synthetic or naturally occurring organic compound. The proteins can include cytokines, growth factors, antibodies, mABs, single chain (scFv) antibodies, or hormones, or the combination thereof, or any other protein molecules having other known functions. Although referred to primarily with respect to treatment of disease, it should be understood that in some cases delivery is of a diagnostic to a site which is diseased, or potentially diseased, for diagnostic or prognostic reasons.

The acyl bond connecting Z—CINN and —$X_1$A is susceptible to hydrolysis and energy activation. Absent energy activation, the acyl bond is stable for up to several days at approximately neutral pH. This property makes the cinnamate based compounds of the present invention useful for therapeutic applications and can serve as a prodrug carrier if desired which releases the enzyme in vivo with or without light activation. The prodrug can be used with a pharmaceutically acceptable carrier for administration to a patient.

B. Preferred Z Groups

In some specifically preferred embodiments, Z is $NR_7R_8$ with $R_7$ being $CH_3CH_2$ and $R_8$ being —$(CR_9R_{10})_n$—$NR_{22}$—$R_{11}$, n being 2, and $R_9$ and $R_{10}$ are both H. $R_{11}$ is preferably L-B so that the prodrug can include a targeting mAb, polymer or both. Reference is also made to commonly assigned U.S. patent application Ser. No. 10/066,323, filed concurrently herewith, the contents of which are hereby incorporated herein by reference.

C. Preferred L-B Groups i. Targeting Molecules

Methods which target a prodrug to a particular site may also be used. For example, U.S. Pat. No. 5,433,955 to Bredehorst et al. describes a two step process in which an activator bound to a targeting moiety is first administered to a subject, then in a second step, the prodrug is released into the circulation and becomes activated only where the activator is bound. Monoclonal antibodies are widely used for selective targeting to particular cells or diseased tissue. For example, a variety of monoclonal antibodies that recognize tumor associated cell-surface antigens have been used as targeting molecules for many of the clinically used anticancer agents. Surface active enzyme coupled to an antibody can also be used to effectuate the drug delivery process. This antibody-enzyme conjugate does not require internalization. One example of a surface active enzyme that has been used as an antibody conjugate is phospholipase-C, which attacks the phospholipids of all cell membranes directly without requiring internalization. Another surface active enzyme used as an antibody conjugate is cobra venom factor (CVF), a complement activating enzyme, which, in addition to not needing to be internalized by the cells, is not inherently cytotoxic.

Antibody Directed Enzyme Prodrug Therapy (ADEPT) is a therapy in which an antibody targets an enzyme to the tumor site. After the enzyme has been situated at the tumor, the relatively non-toxic prodrug is given which is converted to the parent drug by action of the appropriate enzyme. For example, U.S. Pat. No. 5,760,072 describes a paclitaxel prodrug which has a paclitaxel portion coupled to a cleavable N-(aliphatic or aromatic)-O-glycosyl carbamate spacer group which has an anti-tumor effect after cleavage. The prodrug can be activated by a hydrolyzing enzyme, an endogeneous enzyme or an exogeneous enzyme. U.S. Pat. No. 5,433,955 describes a method for site-specific in vivo activation of a prodrug in an animal using an activator-targeting moiety conjugate to localize an activator at a predetermined site of use and a prodrug compound that is converted to an active drug in the presence of the activator.

Another representative B moiety is a targeting peptide or protein such as one of antibodies or mABs, hormones, lectins, cytokines, or growth factors binding to specific receptors on the cells to which the prodrug is to be delivered.

ii. Polymers

To further facilitate the prodrug delivery process, $R_{11}$ can comprise a natural polymer, synthetic polymer, synthetic or naturally occurring organic molecule which can be attached to increase solubility or circulating half-life. For example, an activated polyethylene glycol (PEG) or polypropylene glycol (PPG) can be attached to the Z—CINN core molecule. See U.S. Pat. No. 4,179,337 generally and U.S. Pat. No. 5,612,460 which describes inter alia poly(ethylene glycol)-N-succinimidyl carbonate and derivatives thereof. See also, Poly(ethylene glycol) Chemistry and Biological Applications, Harris, et al., 1997 ACS. The contents of each of the foregoing is incorporated herein by reference. Generally, however, an activated MPEG (for example SS-mPEG$_{5000}$, Shearwater Polymers, Inc.) is reacted with an amino-Z—CINN at ~pH 7.0 for 60 minutes. Excess SS-mPEG is quenched with glycylglycine and the mPEG-N—CINN-AP is reacted with a parent compound, e.g. H—$X_1$A, to form the prodrug under appropriate conditions.

More specifically, in order to form polymer conjugates of the invention, $R_{11}$ may comprise a polymer. For example, polymers such as polyalklyene oxides (PAOs) or similar biologically acceptable polymers are converted into activated forms, as that term is known to those of ordinary skill in the art. Thus, one or both of the terminal polymer hydroxyl end-groups, (i.e. the alpha and omega terminal hydroxyl groups) are converted into the same (homo-) or different (hetero-) reactive functional groups that allow covalent conjugation to the Z—CINN as part of $R_{11}$, and, if desired another active or targeting group. Homo- and heterobifunctional polymers such as those available from Shearwater Polymers may also be employed so as to employ both the advantages of the polymer but also the targeting afforded by mAbs. Other substantially non-antigenic polymers are similarly "activated" or functionalized. As an alternative to PAO-based polymers, other substantially non-antigenic or effectively non-antigenic materials such as collagen, glycosaminoglycans, poly-aspartic acid, poly-L-lysine, poly-lactic acid, copolymers of the foregoing including polylactic-polyglycolic acid copolymers, poly-N-vinylpyrrolidone, collagen cross-linked to hydrophilic polymers or any other suitable non-reactive polymer such as polyethylene alcohols can be used. Specifically preferred polymeric groups are mono or bifunctionally activated polyethylene glycol (PEG) based polymers. It will be appreciated by those of ordinary skill that the specific type of activated PEG or other polymer employed will be dependent upon the particular needs of the artisan and the final product desired. It is contemplated that most commercially available activated polymers are useable herein without undue experimentation.

Polymeric groups of any molecular weight range are acceptable. A preferred polymer molecular weight can range from 2,000 Daltons to 200,000 Daltons. A more preferred molecular weight range is between 5,000 to 50,000 D. The most preferred polymer molecular weight range is between 12,000 and 40,000 D, (number average).

D. Preferred $X_1$A Groups

In one exemplary embodiment, —$X_1$A is a synthetic or naturally occurring organic compound such as one of chemotherapeutics, antibiotics, antivirals, antifungals, and diagnostics. In one preferred embodiment, the prodrug composition is a chemotherapeutic agent. In another preferred embodiment, the prodrug composition is an antiviral such as an anti-Human Immunodeficiency Virus (HIV) drug. —$X_1$A can also be a non-enzyme protein such as a cytokine, a peptide, a growth factor, an antibody, mAB, hormone, polysaccharide, nucleic acid molecule or lipid.

A most preferred embodiment is where —$X_1$A is a taxane such as a paclitaxel moiety or docetaxel and the prodrug has the structure of Formula I wherein $R_1$ is $CH_3$, $R_2$, $R_3$, $R_4$, $R_5$ and $R_6$ are H groups, and $R_7$ is $CH_2CH_3$ and $R_8$ is $CH_2CH_2NH_2$.

Anti-cancer drugs include, but are not limited to the following: taxanes, such as paclitaxel or taxotere; camptothecins, such as camptothecin, CPT 11, irinotecan, topotecan or HCl; podophyllotoxins, such as teniposide; vinblastine sulfate; vincristine sulfate; vinorelbine tartrate; procarbazine HCl; cladribine, leustatin; hydroxyurea; gemcitabine HCl; leuprolide acetate; thioguanine; purinethol; florouricil; anthracyclines, such as daunorubicin or doxorubicin (adriamycin); methotrexates; p-aminoaniline mustard; cytarabine (ara-C or cytosine arabinoside); ; etoposide; bleomycin sulfate; actinomycin D; idarubicin HCl; mitomycin; plicamycin; mitoxantrone HCl; pentostatin; streptozocin; L-phenylalanine mustard; carboplatin derivatives; platinol; busulfan; fluconazole; amifostine; leucovorin calcium and octreotide acetate.

Anti-infective drugs include, but are not limited to the following: nystatin; amphotericin B; fluconazole; metronidazole; aminoglycoside antibiotics, such as amikacin, garamycin, netromycin or streptomycin; cephalosporin antibiotics, such as cefprozil, cephalexin HCl or cefepime; natural, synthetic and semi synthetic macrolide antibiotics, such as clarithromycin or erythromycin salts; chloromycin salts and vibramycin salts.

Other drugs include, but are not limited to the following: asparaginase; arginine deaminase; methioninase; interleukins; interferons and interferon agonists; lipases; esterases; DNA and RNA sequences/oligonucleotides (sense or antisense) and matrix metalloprotease inhibitors.

The biologically active moieties described above are attached to Z—CINN through $X_1$ and are thus capable of forming releasable linkages such as esters, ureas, amides, etc. with Z—CINN. The parent molecule of —$X_1$A, H$X_1$A, therefore has a free hydroxyl group, sulfhydryl group, carboxyl, amino group, etc. capable of reacting with a Z—CINN intermediate resulting in the covalent linkage of the $X_1$A residue to the Z—CINN. A non-limiting sample of suitable —$X_1$A groups include:

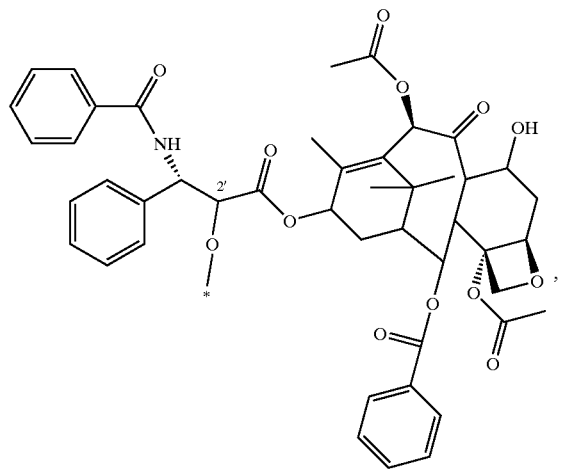

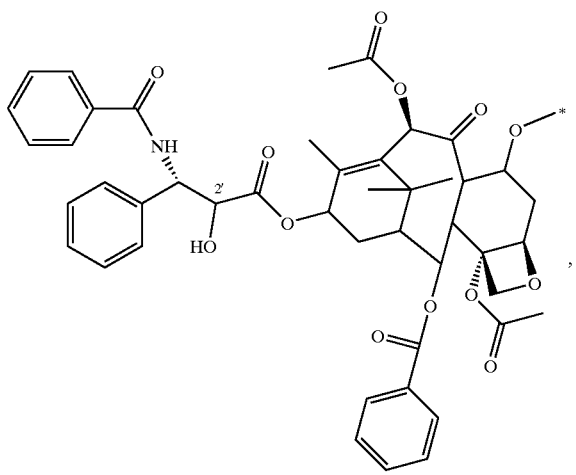

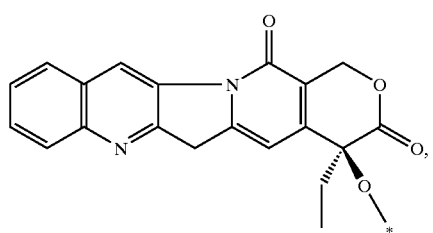

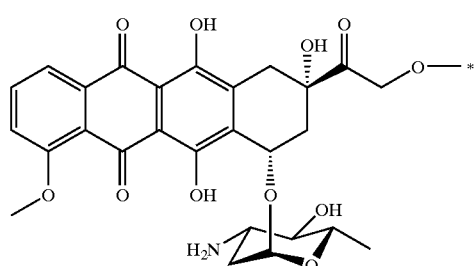

and

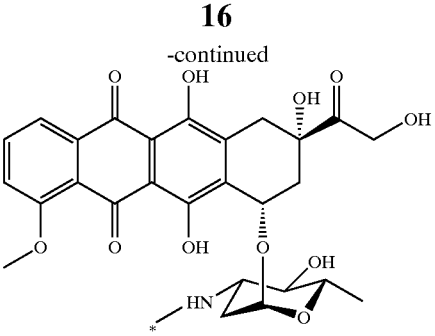

where * represents the point of attachment.

Further specific examples are set forth below:

Targeting Agents (including but not limited to the following):

Any antibody, including murine, that targets a cell or tumor cell in some capacity;

Monoclonal antibodies (mAbs) such as Herceptin® (trastuzumab) with origins from mammals including mice, rats, humans, monkeys, chimeric constructions, etc.;

Single chain antibodies;

These antibodies can be expressed in bacteria, plants, yeast, animals, mammal milk (mouse, goat, sheep, pig, cow, etc), and animal cell cultures including murine, rat, human, hamster, etc.;

Growth factors both natural and recombinant and peptide fractions of growth factors that bind to receptors on the cell surface (EGF, VEGF, FGF, ILGF-I, ILGF-II, TGF)

Interferons both natural or recombinant and peptide fractions of interferons that bind to receptors on the cell surface (IFN-α, β, and γ) and interferon agonists;

Cytokines, either natural or recombinant, and peptide fractions of cytokines that bind to receptor cell surfaces (IL-1, IL-2, IL-3, IL-4, IL-5, IL-6, IL-7, IL-8, IL-9, IL-10, IL-12, IL-15, TNF, etc);

Any peptide, natural, recombinant, or synthetic that binds to a cell surface receptor;

Any hormone either natural or synthetic that binds to a cell surface receptor (estrogen, pro-estrogen);

Any metabolite either natural or synthetic that binds to a cell surface receptor (amino acids, sugars, vitamins, nucleotide, nucleoside);

Any lectin either natural or recombinant that binds to the tumor cell surface;

Sugar peptides either phosphorylated or non-phosphorylated (MDP, MTP, DDP, DTP) or sugar-peptide-lipid targeting agent (monophosphoryl Lipid A, diphosphoryl-Lipid A, DPG-DDP, DPG-DTP, etc.);

Polyethylene glycol polymers and derivatives (2,000→200,000 Daltons);

Poly-aspartic or glutamic acids or poly-lysine amino acid polymers or mixtures of these or other amino acids;

Inhibitors (peptides or chemical; covalent binding or non-covalent binding) of cell surface enzymes (matrix metalloproteinases inhibitors, tyrosine kinase inhibitors, serine protease inhibitors, casein kinase inhibitors, plasminogen activator inhibitors); and glycosaminoglycans and dextrans.

As will be apparent to those skilled in the art, those targeting agents not specifically mentioned, but falling within the above categories, are also within the scope of the present invention.

Thus, in one aspect of the invention, preferred $R_{11}$ substituents are proteins such as antibodies to biological materials, which can be used to assist in the localizing of potential enzyme activity prior to release by light or other energy source.

E. Carriers

Means for delivery of drugs are well known. Many suitable carriers for systemic, local or regional delivery are available to those skilled in the art and may be identified by reference to any textbook on drug carriers or delivery. However, certain carriers may be preferred, for example, carriers which enhance uptake or transport through lipid membranes (such as liposomes) may be preferred in some cases, while other carriers such as poly(lactic acid-glycolic acid) copolymers may be preferred for slow release. The formulation, for example, a small particulate formulation for pulmonary delivery, or encapsulated within an enteric coating for delivery to the lower gastrointestinal tract, may be required in some cases. See, for example, U.S. Pat. No. 6,099,864 and references therein relating to encapsulation into microcapsules or liposomes. The prodrug compositions disclosed herein can be administered in any form of delivery desirable for a particularly disease and the biologically active drug. In another embodiment, the prodrug is formulated in microcapsules or liposomes for delivery.

In one embodiment, the carrier is selected from among intravenous formulations, liposomes, microcapsules, enteric coated formulations, and formulations for pulmonary administration.

IV. Methods of Use/Treatment

The prodrug compounds disclosed herein have many applications. One general application of pharmaceutical importance uses the bifunctional aspect of the cinnamate backbone to achieve not only the targeting, but also the ability to substantially delay release of the therapeutic parent compound until the prodrug is exposed to a source of energy. Since the Z—CINN portion serves as a platform upon which to deliver a myriad of active ingredients, the present invention also provides methods of treatment for various medical conditions in mammals. The methods include administering to the mammal in need of such treatment, an effective amount of a composition of the invention, as described herein, such as a prodrug of doxorubicin to a mammal in need of such treatment.

The prodrug compositions are useful for, among other things, treating diseases which are similar to those which are treated with the parent compound, e.g. neoplastic disease, reducing tumor burden, preventing metastasis of neoplasms and preventing recurrences of tumor/neoplastic growths in mammals. The amount of the prodrug that is administered will depend upon the amount of the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, intensity and duration of light or energy, the presence or absence of a polymer, etc. Those skilled in the art will determine the optimal dosing of the prodrug selected based on clinical experience and the treatment indication. Actual dosages will be apparent to the artisan without undue experimentation. The compounds of the present invention are thus administered as part of pharmaceutically acceptable formulations, e.g. as part of parenteral, i.e. intravenous or oral dosage forms as such are known to those of ordinary skill in the art.

The compounds can be used for purification, particularly those that are immobilized and bind selectively with a target molecule under a given set of conditions, by allowing solutions of the targeted enzyme to equilibrate with inhibitor, then washing away solution before releasing free enzyme following energy input. For example, a compound containing 4-aminoiminophenol at the "A" position could be immobilized and used to isolate thrombin from solution.

The compounds can be used in diagnostic assays. The diagnostic assay may be manual or automated, useful either in laboratories or in the form of a kit.

V. Methods of Synthesis

In another aspect of the invention there are provided methods of preparing the conjugates described herein. Some preferred methods include reacting a cinnamic acid derivative of the formula (IV)

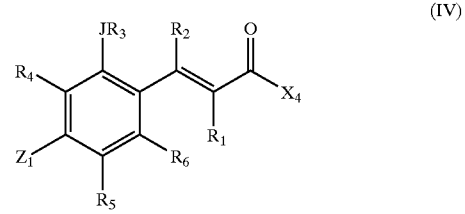

(IV)

wherein all variables are as previously described in Formula (I) and $X_4$ is a reactive terminal group such as OH, NH. SH, halogen, e.g., fluorine, chlorine, bromine, iodine, or other reactive groups known in the art, including, without limitation, aldehydes, hydrazines, carbazates, tosyl, mesyl, paranitrophenyl, N-hydroxysuccinimidyl, maleimidyl, etc; and $Z_1$ is H or

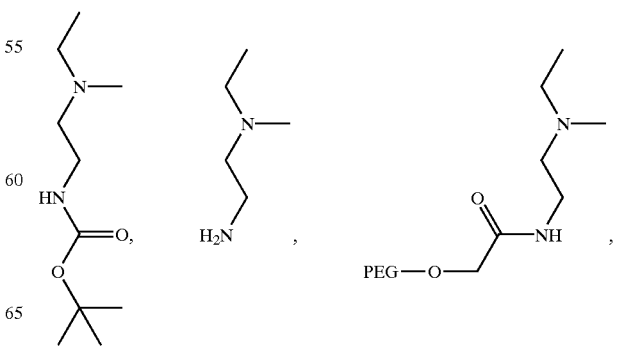

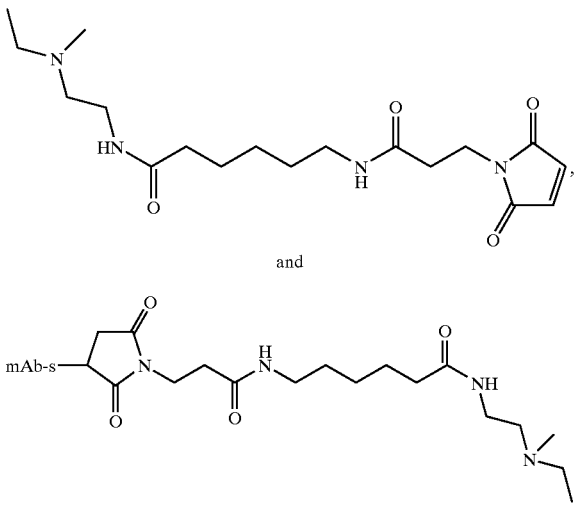

with a biologically active moiety (HX₁A) under conditions sufficient to cause covalent attachment of said biologically active moiety to said cinnamic acid derivative.

Figure 2:
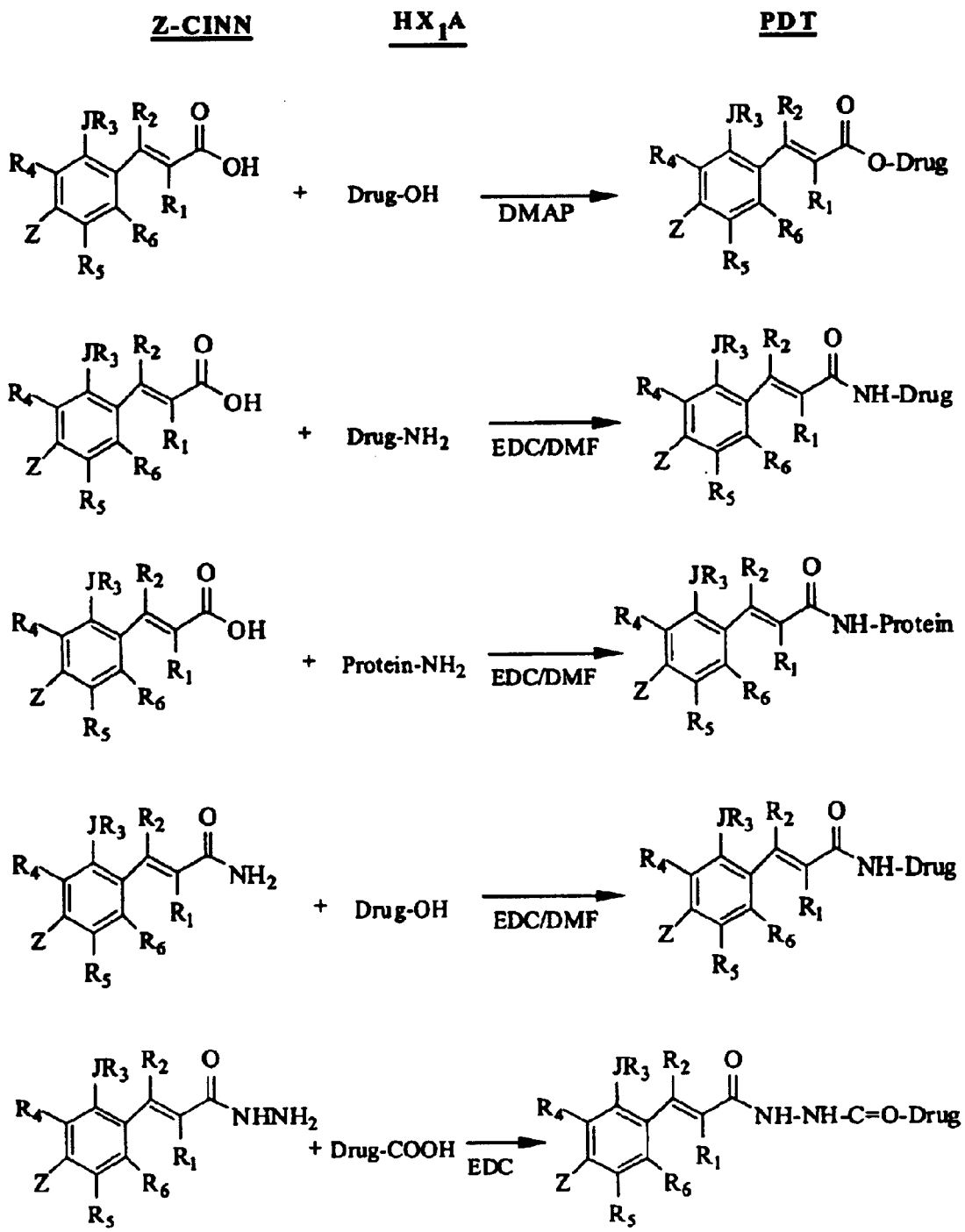
Figure 3:
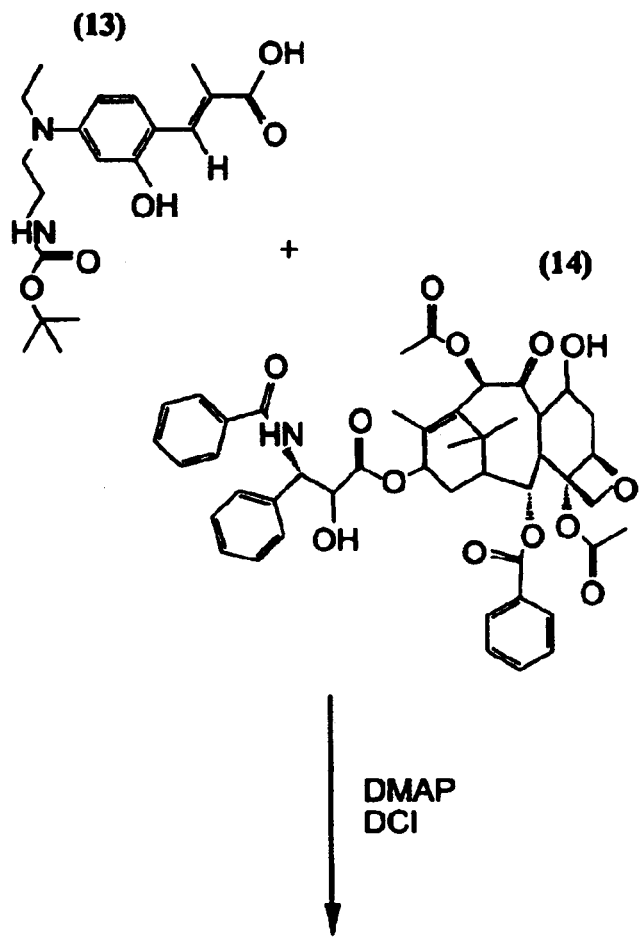
Figure 3:
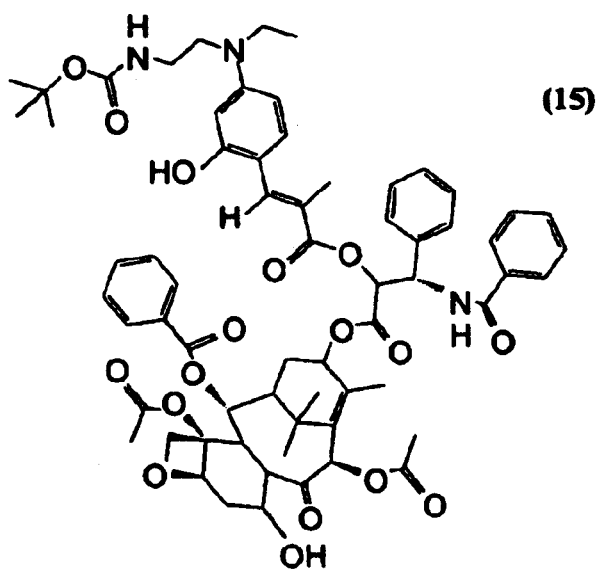

The synthesis of the disclosed Z—CINN—X₁A compositions can be achieved through an acylation reaction of a biologically active molecule (HX₁A) such as a drug with Z—CINN as shown in FIG. 2. In one embodiment, the combination of the two moieties, Z—CINN and HX₁A, can be achieved through the activation of Z—CINN with dicyclohexylcarbodiimide in the presence of 4,4-dimethylaminopyridine, followed by attack on HX₁A to form an ester or amide bond. In another embodiment, the combination of the two moieties, Z—CINN and HX₁A, can be achieved through the coupling of either a cinnamate halide or anhydride or cinnamic acid with a biologically active molecule (HX₁A) such as a drug having a hydroxyl group in the presence of a dehydrating agent such as a base or a mixture of bases, generating the prodrug composition . In another embodiment, Z—CINN and HX₁A can be combined through the coupling of a cinnamate acid with the halide, tosylate or mesylate form of HX₁A in the presence of a base or a mixture of bases, such as triethylamine or a mixture of bases containing the same, to generate the prodrug composition. In still another embodiment, the cinnamate moiety and HX₁A can be combined through a direct coupling of Z—CINN with HX₁A having a free hydroxyl group in the presence of a base or a mixture of bases, such as triethylamine or a mixture of bases containing the same, to generate the prodrug composition. As an example, FIG. 3 illustrates the synthesis of a paclitaxel prodrug (15) using Z—CINN (13). 13 was allowed to react with paclitaxel (14) in CH₂Cl₂, in the presence of diisopropyl-carbodiimide and ditheylaminopyridine, to give 15. Hydrolysis of 15 yields 16.

Figure 4:
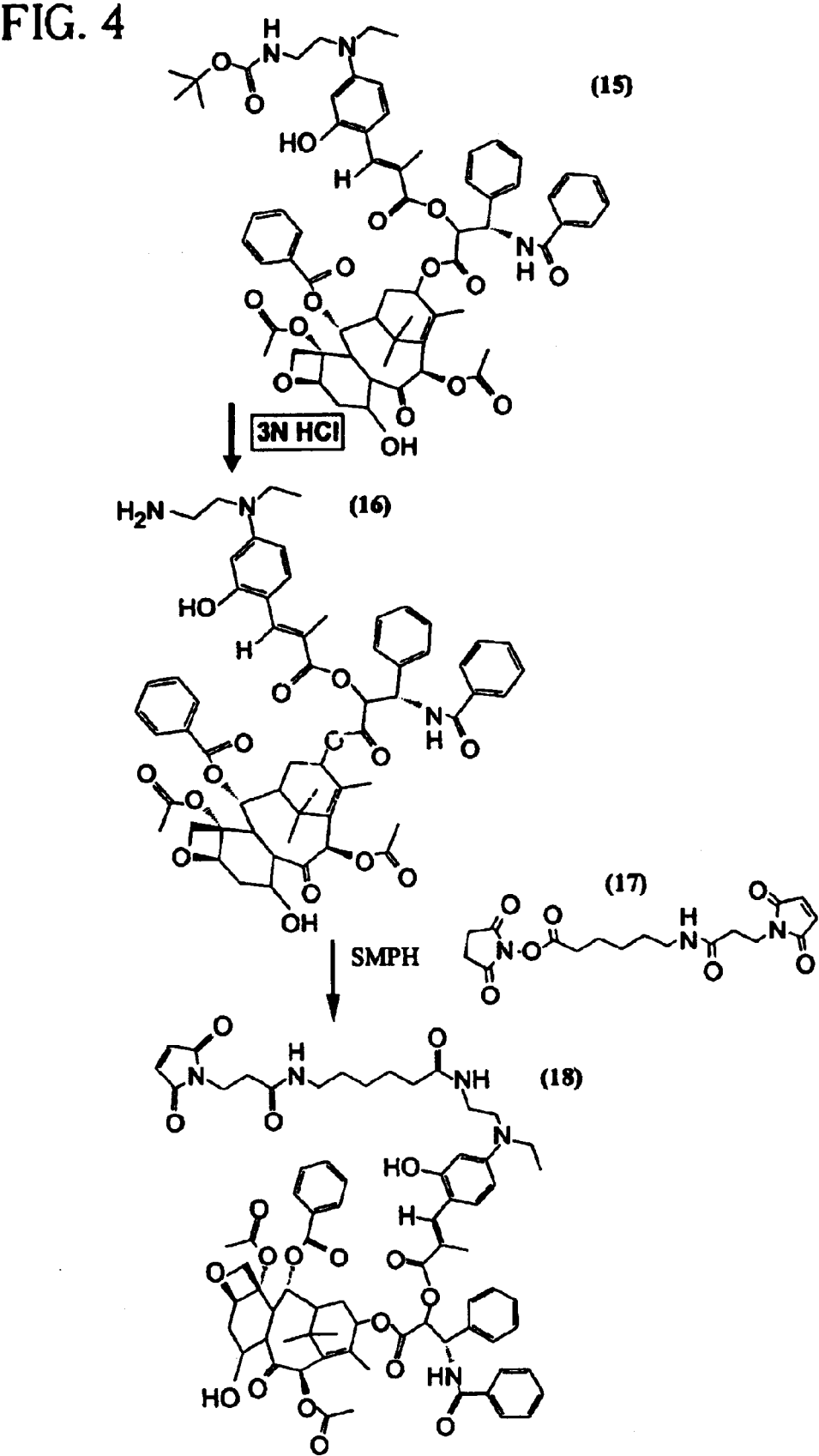
Figure 5:
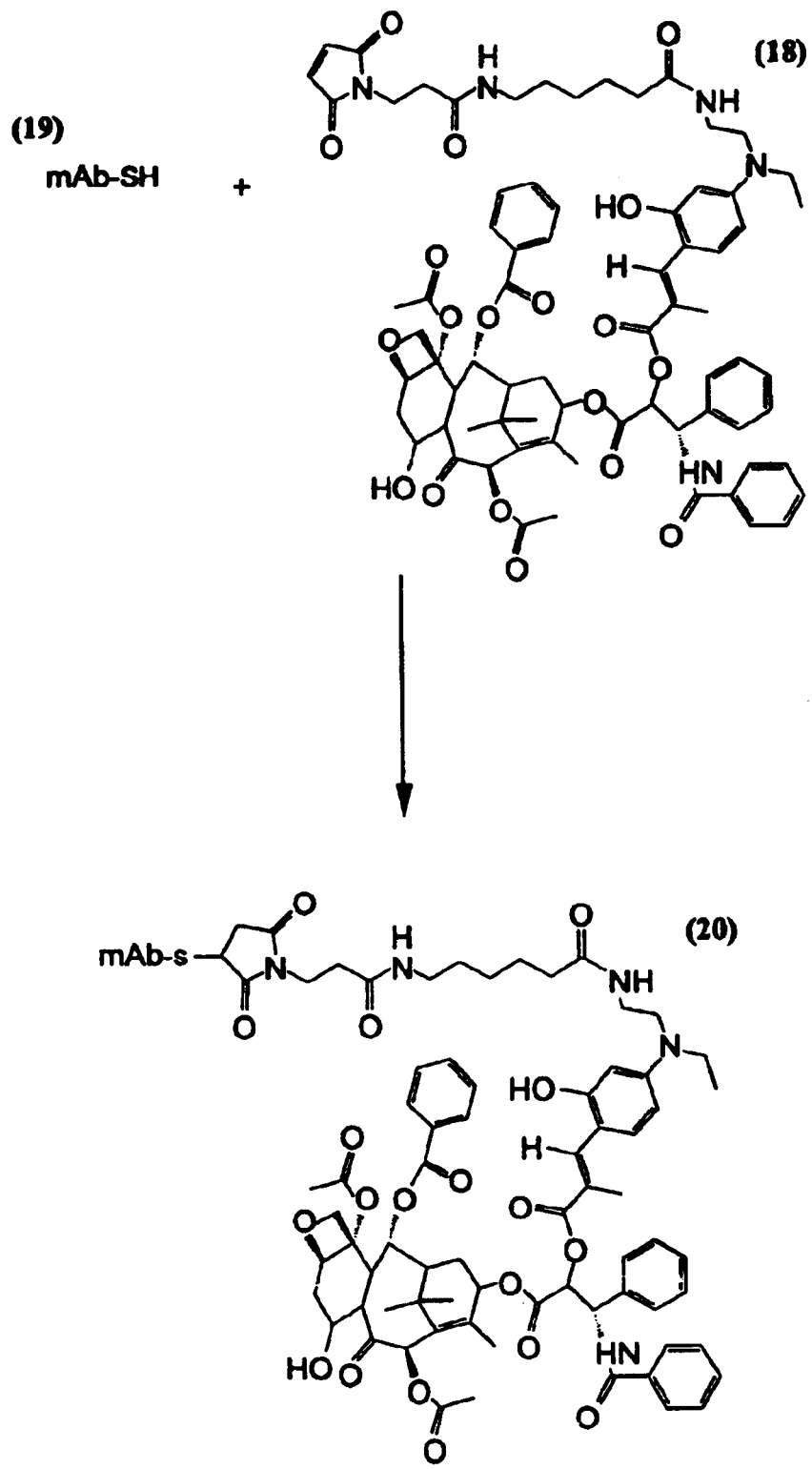

The B or B-L moiety can be attached to Z—CINN as shown in FIG. 4. The attachment of a B or B-L moiety to Z—CINN generally involves coupling Z—CINN—X₁A (15 with B or B-L (SMPH; 17) at neutral pH, generating B-L-Z—CINN—X₁A (18). 18 can be further reacted with 19 to give 20, as shown in FIG. 5. Generally, Z—CINN—X₁A must be formed before the reaction with B or B-L. B or B-L can be used in its original form, which carries a reactive group capable of modifying a free amino group, for example (such as N-hydroxysuccinimide) or free sulfhydryl group (such as maleimido). The identification of suitable reaction chemistry is within the skill in the art and can be readily achieved on the basis of knowledge available in the art.

The combination of the B or B-L moiety and Z—CINN can be achieved through the nitrogen atom in the amino group of R₈, which is —(CR₉R₁₀)₂—NHR₁₁. In one embodiment, as FIG. 6 demonstrates, an N-hydroxysuccinimidyl polyethylene glycol ("NHS-PEG-MAL") (21) is allowed to react with Z—CINN—X₁A (16) in buffer at neutral pH to generate a PEG modified Z—CINN—X₁A [B-L-Z—CINN—X—A;(22)]. 22 can be further reacted with 19 to form 23.

VI. Energy Activation

The energy source to release the biologically active prodrug can be applied externally to the patient or administered internally. The energy source can be in the form of a radiation, magnetic wave, or radiation from a radioactive element. One representative energy source is in the form of light having a wavelength in the range from 300 nm to 450 nm. Another representative energy source is in the form of radiation from a radioactive element such as I*, Tc*, Fe* and Cs*, [* denotes radioactive element].

The energy source can be used to regulate the rate of hydrolysis and release of drug or other HX₁A. Light, as a form of energy, is ideal for the task in that light is highly controllable and clean. Light can be readily applied to a disease site. Light with short wavelength below 300 nm has very poor tissue penetrating ability. Light with a particular wavelength can be used to activate a particular prodrug or other Z—CINN—X₁A, depending on the absorbance spectrum of the conjugate to be activated. The intensity of the light and the duration of application can be used to control the amount of HX₁A to be generated. For example, photoactivity of the prodrug composition of Formula I can be modified by using either electronically withdrawing substituents or electronically donating substituents to modify Z—CINN. For example, modification of Z—CINN with electronically donating groups such as amino or alkoxy groups can effectively shift the activation energy to a radiation with longer wavelength. On the other hand, modification of Z—CINN with electronically withdrawing groups can effectively shift the activation energy to a radiation with shorter wavelength. One skilled in the art will be able to determine which type of light to use, what intensity and what duration are needed, in order to release a pharmaceutically effective drug from the prodrug or release other HX₁A from Z—CINNX₁A.

Energy sources other than visible light can be used, for example, ultraviolet, infrared (for example Ti-Sapphire laser), ultrasound, microwave, electric force, or any radiation generated by radiation source such as Co*, U*, I*, C*, Fe* and Cs* and Tc*.

One preferred embodiment is wherein the energy source is Fe*. Another preferred embodiment is wherein the energy source is Co*. Still another embodiment is wherein the energy source is I*. The activation energy can be directed to the target area from a location outside the body. In the alternative, the activation energy can be administered into a body to activate Z—CINN—X₁A in the disease area. In one embodiment, the prodrug composition is first administered to a mammalian body such as human body. Another composition containing a desired amount of radioactive material is then administered into the human body. The radiation from the radiation active material subsequently activates the cinnamic backbone of the prodrug composition and thus hydrolyzes the prodrug to form a biologically active molecule.

VII. EXAMPLES

The bold-faced numbers recited in the examples correspond to those shown in FIGS. 3–6. FIGS. 7–10 provide the in vivo data corresponding to Example 6.

Example 1

Preparation of tBOC-N—CINN-paclitaxel (15)

Refer to FIG. 3. 3-[2-hydroxy-4-(ethyl)(2-tert-butyloxycarbamidoethyl)-amino]phenyl-2-methyl-2-propenoic acid (13; tBOC-N—CINN; 0.0325 mmoles) was dried for 12–16 hours under vacuum. Dry dichloromethane (5 ml) was added to 13 and the solution was stirred under argon at 4° C. Paclitaxel (14 KLT Labs, Inc.; 0.0325 mmoles) was dissolved in 5 ml of dry dichloromethane and added to 13. 1,3 dicyclohexylcarbodiimide (0.036 mmoles) and 4-dimethylaminopyridine (DMAP; 0.00325 mmoles) were added, and the flask was flushed with argon, warmed to ambient temperature and stirred for 168 hours. The reaction mixture was filtered. The mixture was dried under vacuum, resuspended in chloroform and purified by flash chromatography on silica gel 60 using chloroform, 1% methanol, 2% methanol and 3% methanol (all in chloroform) step gradient to elute the product, tBOC-N—CINN-paclitaxel (15).

Example 2

Preparation of Mal-L-N—CINN-paclitaxel (17)

Refer to FIG. 4. tBOC-N—CINN-paclitaxel (15; 0.0024 mmoles) was resuspended in 1 ml of 3 N HCl and stirred at ambient temperature for 3 hours to hydrolyze the tBOC group and yield N—CINN-paclitaxel (16). The reaction was neutralized with 3N NaOH to give pH 7.2±0.2. 16 (0.0024 mmoles, 2 ml) was mixed with 1 ml of 200 mM sodium phosphate buffer pH 7.4 and 0.0027 mmoles of succinimidyl-[β-maleimidopropionamido]hexanoate (SMPH; Pierce; 17) dissolved in 1 ml of DMSO. The reaction mixture was rocked for two hours at ambient temperature. The reaction was stopped by the addition of 0.1 ml of 100 mM glycylglycine. The Mal-L-N—CINN-paclitaxel (18) was used within two hours.

Example 3

Preparation of Trastuzumab-L-N—CINN-paclitaxel (19)

Refer to FIG. 5. A monoclonal antibody, Herceptin® (trastuzumab, Genentech), was prepared at 5 mg/ml in 50 mM phosphate-0.15 M NaCl buffer, pH 7. SATA (N-succinimidyl S-acetylthioacetate; Pierce) was dissolved in DMSO and a 20-fold molar excess was added to the antibody and reacted for 1 hour. Hydroxylamine HCl (Sigma; 0.5 M in phosphate-NaCl buffer, neutralized to pH 7.0) was added for 60–90 minutes, and antibody (trastuzumab-SH 19) was separated from low molecular weight material by chromatography on D-SALT polyacrylamide desalting columns (Pierce) equilibrated in phosphate-NaCl buffer. Incorporation of thiols into antibody (antibody-SH) was determined using Ellman's reagent (Pierce). Mal-$L_1$—N—CINN-paclitaxel (18), at a 2-fold molar excess to incorporated —SH groups, was added to trastuzumab-SH (19) for 2 hours at pH 7.4 and ambient temperature to give trastuzumab-$L_1$—N—CINN-paclitaxel (20). Antibody-containing fractions (20) were separated from excess 18 on a D-SALT column (Pierce) equilibrated with 50 mM sodium phosphate, 150 mM NaCl, pH 6.5. 20 was concentrated to 5 mg/ml protein using Centricon YM-30 membranes (Millipore), filtered through a 0.22 μm filter (Gelman Sciences, Supor Acrodisc 25), and stored in amber glass vials at 4° C. until used. 20 is referred to as A—Z—CINN 310 in Example 6.

Example 4

Preparation of Mal-L2-N—CINN-paclitaxel (22)

Figure 6:
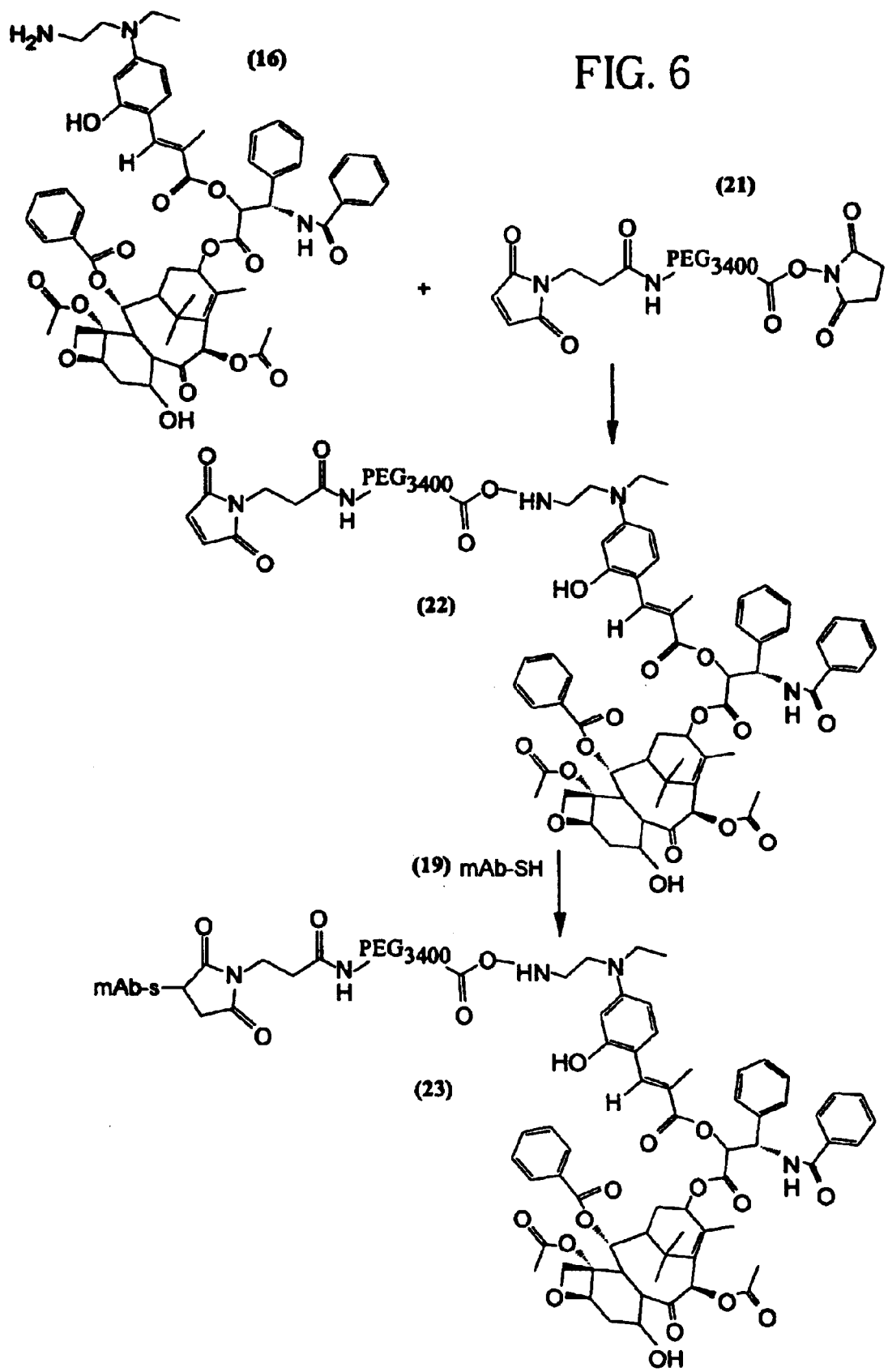

Refer to FIG. 6. tBOC-N—CINN-paclitaxel (15; 0.0024 mmoles) is resuspended in 1 ml of 3 N HCl and stirred at ambient temperature for 3 hours to hydrolyze the tBOC group and yield N—CINN-paclitaxel (16). The reaction is neutralized with 3N NaOH to give pH 7.2±0.2. 16 (0.0024 mmoles, 2 ml) is mixed with 1 ml of 200 mM sodium phosphate buffer pH 7.4 and 0.0027 mmoles of NHS-$PEG_{3400}$-MAL (Shearwater Polymers, Inc. NHS-Mal-3400) dissolved in 1 ml of DMSO. The reaction mixture is rocked for two hours at ambient temperature. The reaction is stopped by the addition of 0.1 ml of 100 mM glycylglycine. The Mal-L2-N—CINN-paclitaxel (22) is used within two hours.

Example 5

Preparation of Trastuzumab-$L_2$-N—CINN-paclitaxel (23)

Refer to FIG. 6. Trastuzumab-SH (19) is prepared as described in Example 3. Mal-$L_2$-N—CINN-paclitaxel (22), at a 2-fold molar excess to incorporated —SH groups, is added to trastuzumab-SH (19) for 2 hours at pH 7.0 and ambient temperature to give trastuzumab-L2-N—CINN-paclitaxel (23). Antibody-containing fractions (23) were separated from excess 22 on a D-SALT column (Pierce) equilibrated with 50 mM sodium phosphate, 150 mM NaCl, pH 6.5. 23 is concentrated to 5 mg/ml protein using Centricon YM-30 membranes (Millipore), filtered through a 0.22 μm filter (Gelman Sciences, Supor Acrodisc 25), and stored in amber glass vials at 4° C. until used. The $PEG_{3400}$ in this example is illustrative of PEGs of any molecular weight within the ranges described in the detailed description section. The molecular weight of the PEG has no effect on the formation of the final compound.

Example 6

Efficacy of Trastuzumab-L-N—CINN-paclitaxel in Targeted Drug Delivery in Tumor-Bearing Mice In this example, BT-474 human mammary tumor cells (Her2+; American Type Culture Collection, Rockville, Md.) were grown in RPMI-1640 medium supplemented with 10% FBS and 2 mM L-glutamine. Young, adult female scid mice were obtained from the Frederick Cancer Research and Development Center (Frederick, Md.). They were housed in plastic microisolator cages with sterile hardwood bedding, fed a standard laboratory diet with filtered tap water ad libitum, and kept at a controlled temperature, humidity, and light cycle. The mice were quarantined two weeks before use.

An estradiol pellet (0.72 mg, 60 day release) was implanted subcutaneously (sc) in each animal 1 day before tumor implantation. BT-474 cells ($1\times10^7$ cells) were mixed with Matrigel® and implanted sc in the mice in 0.2 ml. At 9 days, tumor volumes were ~200 mm$^3$. The mice were divided into 6 groups. All groups received drug via i.v. tail vein injection as a single bolus of 0.2 ml. The first group (4 mice) was the saline control. The second group (4 mice) received 1.0 mg of Herceptin and 0.023 mg of paclitaxel (unlinked; systemic treatment). The third group (4 mice) received 0.1 mg of Herceptin linked to 0.0023 mg paclitaxel (A—Z—CINN 310.1). Group 5 (6 mice) received 0.5 mg of Herceptin linked to 0.012 mg paclitaxel (A—Z—CINN 310.5). Group 6 (6 mice) received 1.0 mg Herceptin linked to 0.023 mg paclitaxel (A—Z—CINN 310). Doses were derived from a 5 mg/ml A—Z—CINN 310 stock solution via dilution into phosphate buffered saline). Groups 1–3 were control groups and did not receive light activation. Groups 4–6, after 6 hours of targeting time, received 65 minutes light exposure/mouse as follows. Six hours post injection, mice to be light treated were anesthetized with Ketamine/Rompun mixture. A 16G needle created a hole in the skin near the tumor; a fiber optic probe was inserted to the edge of the tumor. Tumors were exposed to 5 min of white light at ~0.5 mW/cm$^2$ from a 150 W halogen bulb. This represents active release of drug. All animals were kept under red light conditions for 72 hours post injection, and then returned to their normal 12-hour light/dark cycle.

Mouse survival was observed daily. Tumors were measured twice weekly by caliper in two dimensions, and the measurements were converted to tumor volume. On day 33 post treatment mice were euthanized, tumors were excised and fixed in neutral buffered formalin, embedded in paraffin, sectioned and stained with haematoxylin and eosin (H&E) for histological evaluation. Herceptin-L-N—CINN-Paclitaxel (5) at varying doses, and unlinked Herceptin+ paclitaxel at the highest dose were treatments. Mice received light, or not, as described above. Saline was used as control. All treatment groups showed reduction in tumor volume and tumor cell number; this was seen more rapidly and extensively in samples which received light exposure. Reference is also made to FIGS. 7–10 and the following data.

| Treatment | Trastuzum | Paclitaxel |
|---|---|---|
| A-Z-CINN 310.1 | 0.1 mg | 0.0023 mg |
| A-Z-CINN 310.5 | 0.5 mg | 0.012 mg |
| A-Z-CINN 310 | 1.0 mg | 0.023 mg |
| Systemic Therapy | 1.0 mg | 0.023 mg |

Figure 7:
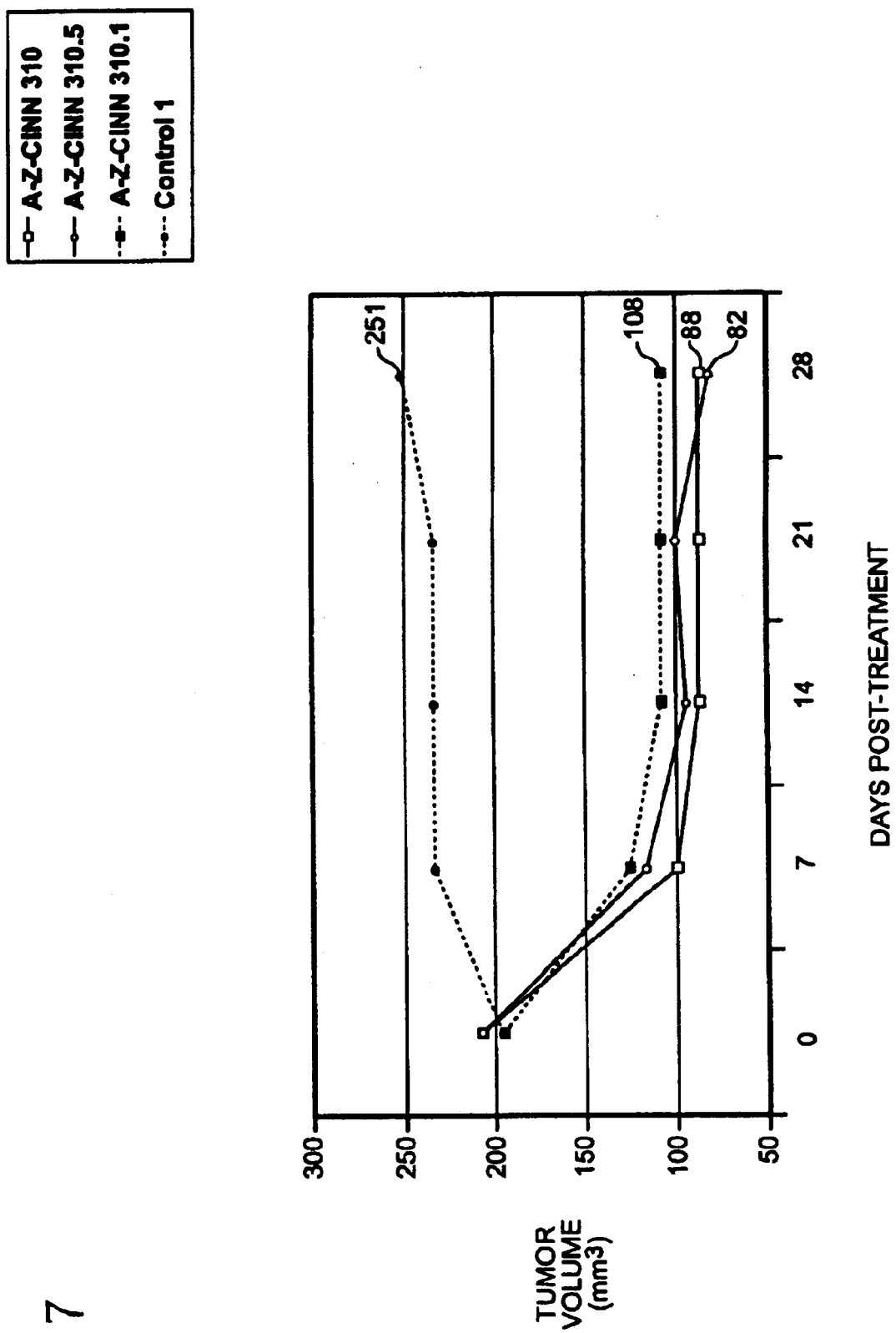

FIG. 7 shows the effects of does-dependent light release of targeted A—Z—CINN 310 (20) over non-treated control tumors. In all cases where A—Z—CINN compositions were employed, tumor mass shrunk 45–60% by day 28 in a dose-dependent fashion with active release of the drug. There was aggressive shrinkage by day 7 and no tumor regrowth was seen.

Figure 8:
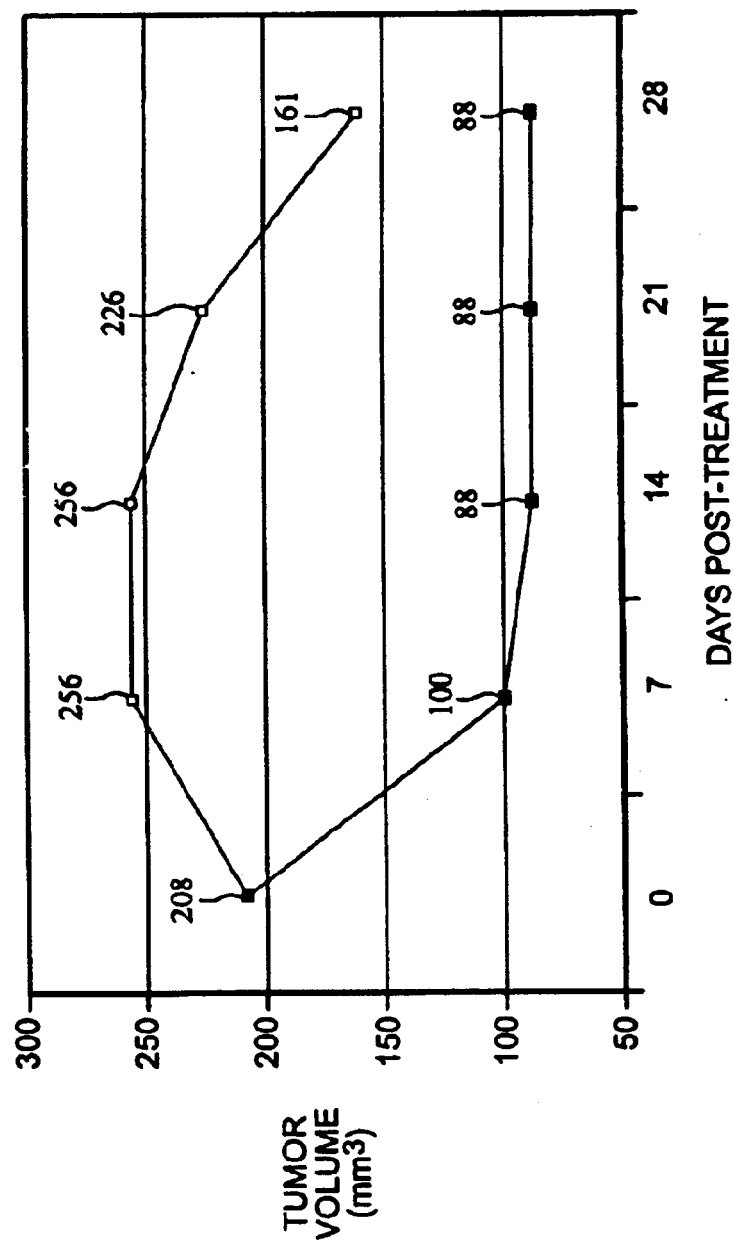

In FIG. 8, active release is compared to systemic therapy. The advantages of this, including the compounds of the present invention, are apparent. Tumor mass shrunk by 45% with A—Z—CINN 310 followed by light release versus 22% with systemic therapy, in spite of the fact that the amount of trastuzumab and paclitaxel administered was the same.

Figure 9:
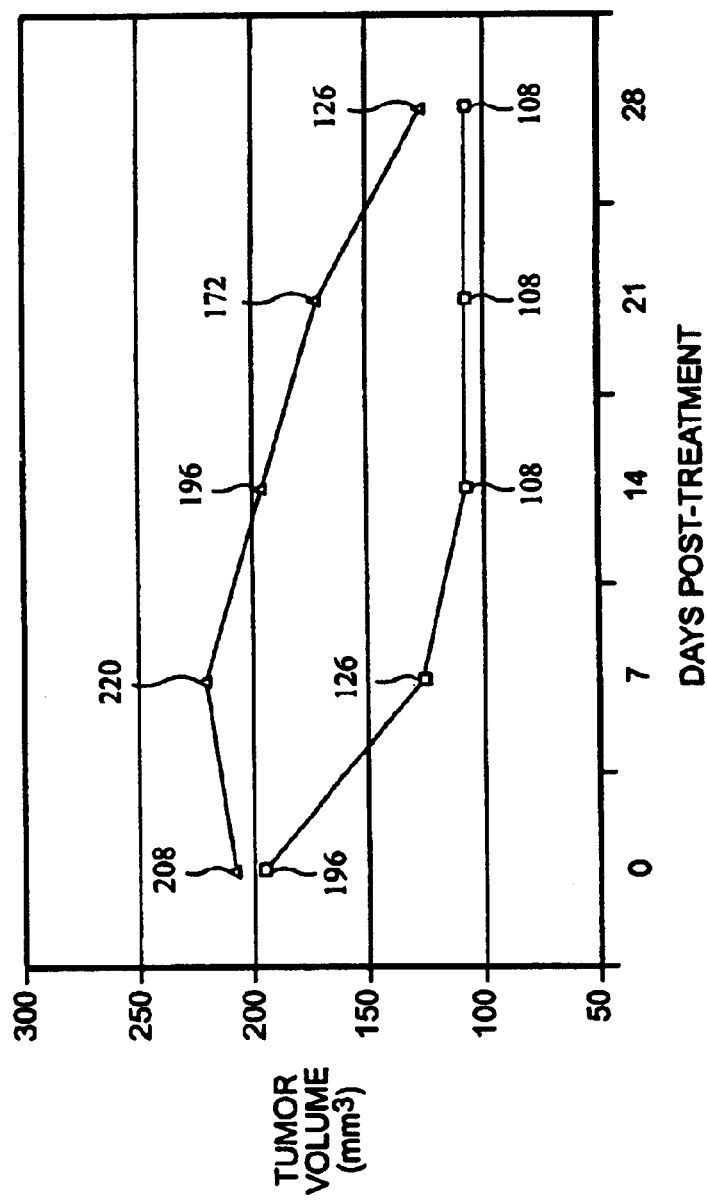

In FIG. 9, a comparison of release of paclitaxel via hydrolysis and active release is illustrated. It can be seen that by day 28, the amount of tumor mass shrinkage is about the same. The advantages of active light release are most apparent, however, at about seven days post treatment.

Figure 10:
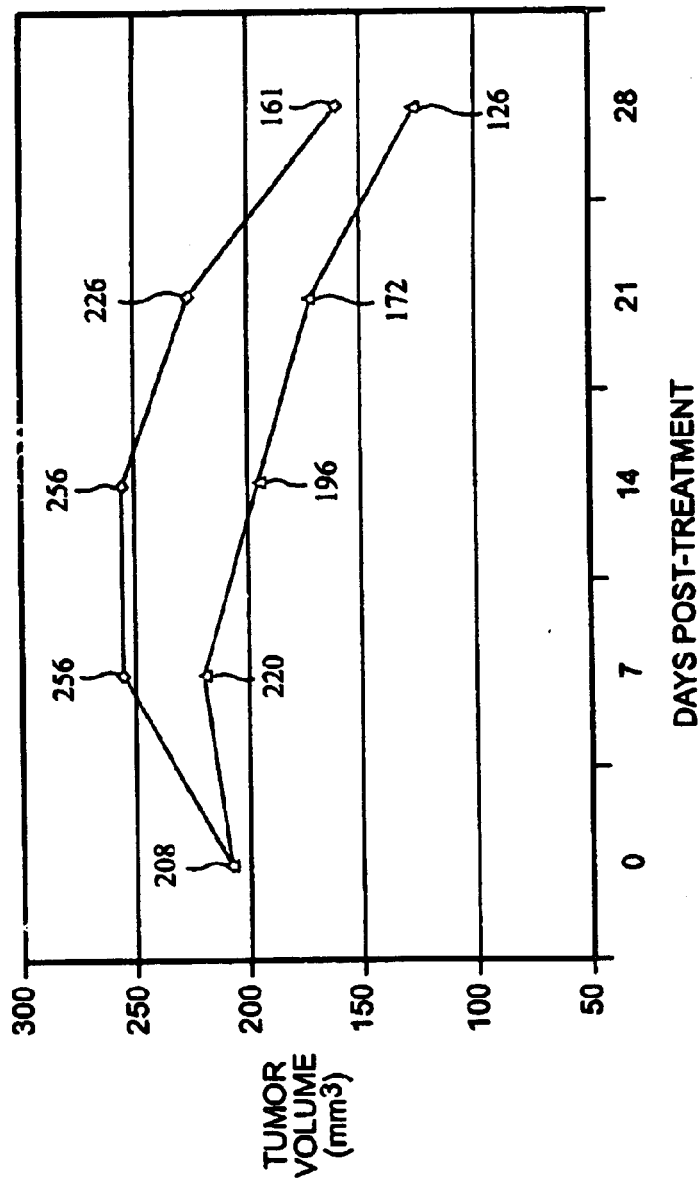

Finally, in FIG. 10, a comparison of drug release via hydrolysis from A—Z—CINN was compared to systemic therapy, i.e. administration of the same agents without the use of the novel prodrug carrier system. It can be seen that employment of the A—Z—CINN carrier provides immediate and constant advantages in shrinkage of tumor volume when compared to systemic therapy. In this experiment, the amount of Herceptin and paclitaxel in A—Z—CINN 310 was 10% of the amount of Herceptin and paclitaxel in the unlinked, systemic treatment, indicating amplified benefits with targeted drug delivery.

Example 7

Lung Cancer

A. Preparation of Antibody-Linker-CINN-Drug and Its Use tBOC-N—CINN acid (13, 0.0325 mmoles) is dried over night under vacuum. Dry dichloromethane (5 ml) is added to 13 and the solution is stirred under Argon at 4° C. Paclitaxel (14 KLT Labs, Inc., 0.0325 mmoles) is dissolved in 5 ml of dry dichloromethane and added to 13. DMAP (4-dimethylamino pyridine, 0.00325 mmoles) and 1,3 dicyclohexylcarbodiimide (0.036 mmoles) are added, the flask is flushed with argon, warmed to ambient temperature and stirred for 168 hours. The reaction mixture is filtered and dried under vacuum, resuspended in chloroform and purified by flash chromatograph on silica gel 60 using chloroform, 1% methanol, 2% methanol and 3% methanol step gradient to elute the product tBOC-N—CINN-paclitaxel (15).

tBOC-N—CINN-paclitaxel (15, 0.0024 mmoles) is resuspended in 3 N HCl (1 ml) and stirred at ambient temperature for 3 hours. The reaction is neutralized with 3N NaOH to give pH 7.4 solution. A—Z—CINN-paclitaxel (2 ml) is mixed with 1 ml 200 mM sodium phosphate buffer pH 7.4 and 1 ml of 0.0027 mmoles of NHS-PEG$_{3400}$-MAL (21; Shear-water Polymers, Inc. NHS-Mal-3400) dissolved in DMSO. The reaction mixture is rocked for two hours at ambient temperature. The reaction is stopped by the addition of 100 μl of 100 mM glycylglycine. The Mal-PEG$_{3400}$-N—CINN-paclitaxel (22) is used within two hrs.

B. Preparation of Antibody~S-Mal-PEG$_{3400}$-N—CINN-paclitaxel

A murine monoclonal antibody, BR110 (Hellstrom et.al. U.S. Pat. No. 5,840,854) is diluted to 5 mg/ml in phosphate-NaCl buffer, pH 7. SATA (N-succinimidyl S-acetylthioacetate; Pierce) is dissolved in DMSO and a 20-fold molar excess is added to the protein and reacted for 1 hour. Hydroxylamine HCl (Sigma; 0.5 M, neutralized to pH 7.0) is added for 60–90 min, and antibody is separated from low molecular weight material by chromatography on D-SALT Polyacrylamide desalting columns (Pierce) equilibrated in phosphate-NaCl buffer. Incorporation of thiols into the murine antibody (antibody-SH; 20) is determined using Ellman's reagent (Pierce). Mal-PEG$_{3400}$-N—CINN-paclitaxel 22 at a 2-fold molar excess to incorporated —SH groups, is added to BR110-mAb-SH for 2 hours at pH 7.4 and ambient temperature to give BR110-mAb-S-Mal-PEG$_{3400}$-N—CINN-paclitaxel 23. Antibody-containing fractions 23 (BR110-mAb-S-Mal-PEG$_{3400}$-N—CINN-paclitaxel) are separated from excess Mal-PEG$_{3400}$-N—CINN-paclitaxel 22 on a D-SALT column (Pierce) buffered with 50 mM sodium phosphate pH 6.5 and 150 mM NaCl. The antibody-drug 23 (BR110-mAb-S-Mal-PEG$_{3400}$-N—CINN-paclitaxel) is concentrated to 5 mg/ml protein using Centricon YM-30 membranes and sterile filtered (0.22μ filter; Gelman Sciences, Supor Acrodisc 25), and stored in amber glass vials at 4° C. until used to treat a human tumor growing in a mouse.

C. Treatment of Human Lung Carcinoma With A—Z—CINN 441 (BR110-mAb-S-Mal-PEG$_{3400}$-N—CINN-paclitaxel)

MAb BR110 is a murine mAb to a 66-kDa glycoprotein that is found on the cell surface of human lung, colon and breast tumor cells. Human lung carcinoma cell line H2987 is grown in cell culture as described (U.S. Pat. No. 5,840,854). 1×10$^7$ cells/mouse are implanted s.c. into a nude mice. When the tumors reached 150–200 mm$^3$ in size, A—Z—CINN 441 is used to treat the tumor as follows: 0.1–1.0 mg of A—Z—CINN 441 (1 mg mAb protein with ~25 ug paclitaxel covalently attached) is injected i.v. via tail vein into mice with the tumor. After 6 hours, mice that receive 0.1, 0.5 or 1.0 mg of A—Z—CINN 441 are anesthetized with a Ketamine/Rompun mixture. A 16G needle is used to create a hole in the skin and a 1 mm fiber optic probe is inserted up to the tumor. The tumor is exposed to white light for 5 minutes with a power of about 0.5 mW/cm$^2$. Other treatment groups do not receive light treatment. All mice are kept under "red lights" to prevent light activation of the drug, for 72 hours post injection, then returned to normal light/dark cycle. Tumors in groups that receive light treatment shrink immediately (>50% in 7 days) and are not detectable by 28 days. Tumors that are treated with A—Z—CINN— 441 but did not receive light stimulation shrank at a slower pace and are smaller than 50 mm at 28 days. Groups that receive antibody and free drug (unlinked) show tumor growth, and by 28 days the mice either die or have tumors>800 mm$^3$.

Example 8

Colon Cancer

A. Preparation of Antibody-Linker-CINN-Drug

Mal-PEG$_{3400}$-N—CINN-paclitaxel is prepared as described in Example 5A.

B. Preparation of Antibody~Linker-N—CINN-paclitaxel

Antibody~S-Mal-PEG$_{3400}$-N—CINN-paclitaxel is prepared as described in Example 5B, except that mAb A7 is used in place of mAb BR110 to form A7-mAb-S-Mal-PEG$_{3400}$-N—CINN-paclitaxel 23.

C. Treatment of Human Colon Carcinoma With A—Z—CINN 551 (A7-mAb-S-Mal-PEG$_{3400}$-N—CINN-paclitaxel)

Human colon carcinoma cell line LS-180 is grown in cell culture as described (Kinuya et.al. 2001. J. Nucl. Med. 42:596–600). 1×10$^7$ cells/mouse are implanted s.c. into nude mice. When the tumors reached 150–200 mm$^3$ in size, A—Z—CINN 551 is used to treat the tumor as follows; 0.1–1.0 mg of A—Z—CINN 551 (1 mg mAb protein with ~25 ug paclitaxel covalently attached) is injected i.v. via tail vein into mice with the tumor. After 6 hours, mice that received 0.1, 0.5 or 1.0 mg of A—Z—CINN 441 are anesthetized with a Ketamine/Rompun mixture. A 16 G needle is used to create a hole in the skin and a 1 mm fiber optic probe is inserted up to the tumor. The tumor is exposed to white light for 5 minutes with a power of about 0.5 mW/cm$^2$. Other treatment groups do not receive light treatment. All mice are kept under "red lights" to prevent unnecessary light exposure and activation of A—Z—CINN 551 for 72 hours post injection, then returned to normal light/dark cycle. Tumors in groups that receive light treatment shrink immediately (>50% in 7 days) and are less than 50 mm$^3$ by 28 days. Tumors that are treated with A—Z—CINN— 551 but do not receive light stimulation shrink at a much slower pace and are smaller than 100 mm$^3$ at 28 days. Groups that receive antibody and free drug (unlinked) show tumor growth, and by 28 days the mice either die or have tumors>800 mm$^3$.

Example 9

Breast Cancer

A. Preparation of Antibody-Linker-CINN-Drug

Mal-PEG$_{3400}$-N—CINN-paclitaxel is prepared as described in Example 5A.

B. Preparation of Antibody-Linker-N—CINN-Drug

Antibody~S-Mal-PEG$_{3400}$-N—CINN-paclitaxel is prepared as described in Example 5B except that mAb NR-LU 10 is used in place of BR110 to form NR-LU-10 mAb-S-Mal-PEG$_{3400}$-N—CINN-paclitaxel 23.

C. Treatment of Human Breast Carcinoma with A—Z—CINN 361 (NR-LU-10 mAb-S-Mal-PEG$_{3400}$-N—CINN-paclitaxel)

Human breast cancer xenographs are prepared as described (Burak et.al. 1998. Nucl. Med. Biol. 25:633–637) Xenographs are implanted s.c. into a nude mice. When the tumor reached 150–200 mm$^3$ in size, A—Z—CINN 361 is used to treat the tumor as follows; 0.1–1.0 mg of A—Z—CINN 361 (1 mg mAb protein with ~25 ug paclitaxel covalently attached) is injected i.v. via tail vein into mice with the tumor. After 6 hours, mice that receive 0.1, 0.5 or 1.0 mg of A—Z—CINN 361 are anesthetized with a Ketamine/Rompun mixture. A 16G needle is used to create a hole in the skin and a 1 mm fiber optic probe is inserted up to the tumor. The tumor is exposed to white light for 5 minutes with a power of about 0.5 mW/cm$^2$. Other treatment groups do not receive light treatment. All mice are kept under "red lights" to prevent unnecessary light exposure and activation of A—Z—CINN 361 for 72 hours post injection, then returned to normal light/dark cycle. Tumors in groups that receive light treatment shrink immediately (>50% in 7 days) and are less than 50 mm$^3$ by 28 days. Tumors that are treated with A—Z—CINN— 361 but do not receive light stimulation shrink at a much slower pace and are smaller than 100 mm$^3$ at 28 days. Groups that receive antibody and free drug (unlinked) show tumor growth, and by 28 days the mice either die or have tumors>800 mm$^3$.

Example 10

Preparation of tBOC-N—CINN-camptothecin (24)

(13; tBOC-N—CINN; 0.0325 mmoles) was dried for 12–16 hours under vacuum. Dry pyridine (5 ml) was added to 1 and the solution was stirred under argon at 4° C. Camptothecin (Aldrich, 36,563–7; 0.0325 mmoles) was dissolved in 10 ml of dry pyridine and added to 13. 1,3 dicyclohexylcarbodiimide (0.036 mmoles) and 4-dimethylamino-pyridine (DMAP; 0.00325 mmoles) were added, and the flask was flushed with argon, warmed to ambient temperature and stirred for 168 hours. The reaction was filtered and the mixture was dried under vacuum, resuspended in chloroform and purified by flash chromatography on silica gel 60 using chloroform, 1% methanol, 2% methanol and 3% methanol (all in chloroform) step gradient to elute the product, tBOC-N—CINN-camptothecin (24).

Example 11

Preparation of tBOC-N—CINN-doxorubicin (25) Using Dicyclohexylcarbodiimide 13 (tBOC-N—CINN; 0.017 mmoles) was dried for 12–16 hours under vacuum. Dry pyridine (15 ml) was added to 13 and the solution was stirred under argon at 4° C. Doxorubicin hydrochloride (Aldrich, 86-036-0; 0.017 mmoles) was dissolved in 15 ml of dry pyridine and added to 13. 1,3 dicyclohexylcarbodiimide (0.022 mmoles) and 4-dimethylaminopyridine (DMAP; 0.0017 mmoles) were added, and the flask was flushed with argon, warmed to ambient temperature and stirred for 168 hours. The reaction was filtered and the mixture was dried under vacuum, resuspended in chloroform and purified by flash chromatography on silica gel 60 using chloroform, 1% methanol, 2% methanol and 3% methanol (all in chloroform) step gradient to elute the product, tBOC-N—CINN-doxorubicin (25) attached via hydroxyl groups.

Example 12

Preparation of tBOC-N—CINN-doxorubicin (26) Using Dicyclohexylcarbodiimide 13 (tBOC-N—CINN; 0.017 mmoles) is dried for 12–16 hours under vacuum. Dry pyridine (5 ml) is added to 13 and the solution is stirred under argon at 4° C. Doxorubicin hydrochloride (Aldrich, 86-036-0; 0.017 mmoles) is dissolved in 15 ml of dry pyridine and added to 13. 1,3 dicyclohexylcarbodiimide (0.022 mmoles) and MES buffer (4-Morpholinoethanesulfonic acid pH 4.5) are added, and the flask is flushed with argon, warmed to ambient temperature and is stirred for 168 hours. The reaction is filtered and the mixture is dried under vacuum, resuspended in chloroform and purified by flash chromatography on silica gel 60 using chloroform, 1% methanol, 2% methanol and 3% methanol (all in chloroform) step gradient to elute the product, tBOC-N—CINN-doxorubicin (26) attached via amino group on the sugar.

Example 13

Preparation of PEG-N—CINN-cytokine (27)

13 (tBOC-N—CINN; 0.020 mmoles) is dried for 12–16 hours under vacuum. 13 is resuspended in 1 ml 3 N HCl and mixed for three hours at 20° C. The reaction is neutralized with 3N NaOH to give pH 7.2±0.2. 13 (0.020 mmoles, 2 ml) is mixed with 1 ml of 200 mM sodium phosphate buffer pH 7.4 and 0.027 mmoles of NHS-PEG$_{3400}$ (Shearwater Polymers, Inc. NHS-3400) dissolved in 1 ml of DMSO. The reaction mixture is rocked for two hours at ambient temperature. The reaction is stopped by the addition of 0.1 ml of 100 mM glycylglycine. The PEG-N—CINN is used within two hours. A cytokine (IL-2) is obtained and resuspended at 1 mg/ml in 50 mM phosphate-0.15 M NaCl buffer, pH 7. To 83 nmoles of IL-2 (1 mg) 83 nmoles of PEG-N—CINN in buffer plus 124 nMoles of EDC(Pierce, 1-Ethyl-3-(3-dimethylaminopropyl)-carbodiimide hydrochloride) in DMSO. The reaction is stirred overnight. The PEG-N—CINN-IL-2 is separated from low molecular weight material by chromatography on D-SALT polyacrylamide desalting columns (Pierce) equilibrated in phosphate-NaCl buffer.

Many modifications and variations of this invention can be made without departing from its spirit and scope, as will be apparent to those skilled in the art. The specific embodiments described below are offered by way of example only, and the invention is to be limited only by the terms of the appended claims, along with the full scope of equivalents to which such claims are entitled. All publications and patents mentioned herein are incorporated herein by reference.

We claim:

1. A compound comprising the formula:

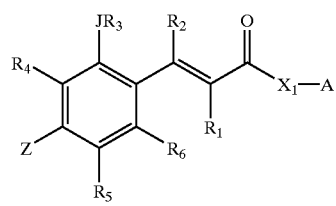

(I)

wherein:

X$_1$A is a residue of a releasable biologically active moiety;

R$_1$ and R$_2$ are individually selected from the group consisting of H, CH$_3$, C$_2$–C$_{10}$ alkyls, C$_2$–C$_{10}$ alkenyls or C$_2$–C$_{10}$ alkynyls, each of which can be substituted or unsubstituted; straight or branched, C$_2$–C$_{10}$ heteroalkyls, C$_2$–C$_{10}$ heteroalkenyls or C$_2$–C$_{10}$ heteroalkynyls and wherein: R$_{15}$ and R$_{16}$ are individually selected from the group consisting of H, CH$_3$, C$_2$–C$_{10}$ alkyls, C$_2$–C$_{10}$ alkenyls or C$_2$–C$_{10}$ alkynyls, each of which can be substituted or unsubstituted; straight or branched; and C$_2$–C$_{10}$ heteroalkyls, C$_2$–C$_{10}$ heteroalkenyls or C$_2$–C$_{10}$ heteroalkynyls;

p is a positive integer from 1 to about 12;

D is selected from among —SH, —OH, X$_2$, —CN, —OR$_{19}$, NHR$_{20}$,

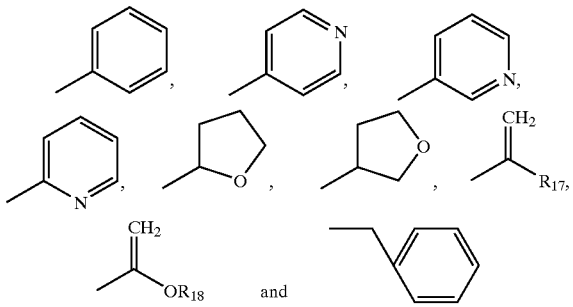

wherein:

R$_{17}$ is H, CH$_3$ or X$_3$;

R$_{18}$ is H, a C$_1$–C$_4$ alkyl or benzyl;

R$_{19}$ is H, a C$_{1-4}$alkyl, X$_2$ or benzyl;

R$_{20}$ is H, a c$_{1-10}$ alkyl or —C(O)R$_{21}$, wherein $R_{21}$ is H, a C1A alkyl or alkoxy, t-butoxy or benzyloxy;

$X_2$ and $X_3$ are independently selected halogens;

$R_3$ is H, $CH_3$, or —C(=O)($CR_{15}R_{16}$)$_w$–D, where w is 0 or an integer from 1 to about 12, and D is H or as described for $R_1$ and $R_2$;

J is O, NH or S;

$R_4$, $R_5$, and $R_6$ are independently selected from the group consisting of H, $CH_3$, $C_2$–$C_{10}$ alkyls, $C_2$–$C_{10}$ alkenyls or $C_2$–$C_{10}$ alkynyls, each of which can be substituted or unsubstituted; straight or branched; $C_2$–$C_{10}$ heteroalkyls, heteroalkenyls or heteroalkynyls and halogens;

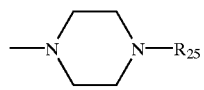

Z is $NR_7R_8$ or wherein $R_7$ is selected from among H, $CH_3$, $C_2$–$C_{10}$ alkyls, alkenyls or alkynyls which can be substituted or unsubstituted; straight or branched; $C_2$–$C_{10}$ heteroalkyls, heteroalkenyls or heteroalkynyls, or —($CR_{23}R_4$)$_q$-aryl, or $R_8$, wherein $R_{23}$ and $R_{24}$ are independently selected from the group consisting of H and $C_1$–$C_{10}$ alkyls;

q is an integer from 1 to about 6;

$R_8$ is selected from the group consisting of ($CR_9R_{10}$)$_n$—$NR_{22}$—$R_{11}$, ($CR_9R_{10}$)$_n$—$CH_2$—NHC(O)$R_{26}$ and ($CR_9R_{10}$)$_n$—$CH_2$-E;

wherein $R_9$ and $R_{10}$ are independently selected from the group consisting of H, $CH_3$, $C_2$–$C_{10}$ alkyls, $C_2$–$C_{10}$ alkenyls or $C_2$–$C_{10}$ alkynyls, each of which can be substituted or unsubstituted; straight or branched; $C_2$–$C_{10}$ heteroalkyls, $C_2$–$C_{10}$ heteroalkenyls or $C_2$–$C_{10}$ heteroalkynyls and halogens;

$R_{26}$ is H, $CH_3$, O-t-butyl, O-benzyl;

E is OH, SH or O—C(O)$R_{27}$, wherein $R_{27}$ is a $C_1$–$C_6$ alkyl, benzyl or phenyl; $R_{22}$ is H or $CH_3$;

n is a positive integer from 1 to about 10;

$R_{11}$ is H or -L-B, wherein L is a linker; and

B is an active moiety, reactive group moiety or a polymer; and $R_{25}$ is H, —C(O)—$R_{28}$ or —C(O)—O—$R_{29}$, wherein $R_{28}$ is a $C_1$–$C_6$ alkyl or benzyl; and $R_{29}$ is $CH_3$, t-butyl or benzyl.

2. The compound of claim 1, wherein $X_1$ is O, NH, or S.

3. The compound of claim 2, wherein said residue of said biologically active moiety is selected from the group consisting of synthetic or naturally occurring organic compounds.

4. The compound of claim 3 wherein said organic compounds are selected from the group consisting of chemotherapeutics, antibiotics, antivirals, antifungals, and diagnostics.

5. The compound of claim 4, wherein said chemotherapeutics are selected from the group consisting of taxanes, taxane derivatives, paclitaxel, paclitaxel derivatives, docetaxel, docetaxel derivatives, camptothecin, camptothecin derivatives, doxorubicin, doxorubicin derivatives, amethopterin, etoposide, irinotecan and fluconazole.

6. The compound of claim 5, wherein said chemotherapeutic is paclitaxel.

7. The compound of claim 2, wherein said residue of said biologically active moiety is selected from the group consisting of proteins, polysaccharides, nucleic acids, cytokines, growth factors, antibodies, mABs, single chain antibodies (scFv), hormones and lipids.

8. The compound of claim 1, wherein Z is $NR_7R_8$.

9. The compound of claim 8, wherein $R_8$ is —$CH_2$—$CH_2$—$NH_2$.

10. The compound of claim 8, wherein $R_8$ is ($CR_9R_{10}$)$_n$—$NR_{22}$—$R_{13}$.

11. The compound of claim 1, wherein L-B comprises a maleimidyl or an N-hydroxysuccinimidyl group.

12. The compound of claim 10, wherein $R_{11}$ comprises a polyalkylene oxide residue.

13. The compound of claim 12, wherein said polyalkylene oxide residue is a polyethylene glycol.

14. The compound of claim 13, wherein said polyethylene glycol has a number average molecular weight of from about 2,000 to about 200,000 daltons.

15. The compound of claim 10, wherein $R_{11}$ comprises a polymer selected from the group consisting of collagen, glycosaminoglycan, poly(-aspartic acid), poly(-L-lysine) poly(-lactic acid), copolymers of poly(-lactic acid) and poly (-glycolic acid) and poly-N-vinylpyrrolidone.

16. A compound of claim 1, selected from the group consisting of:

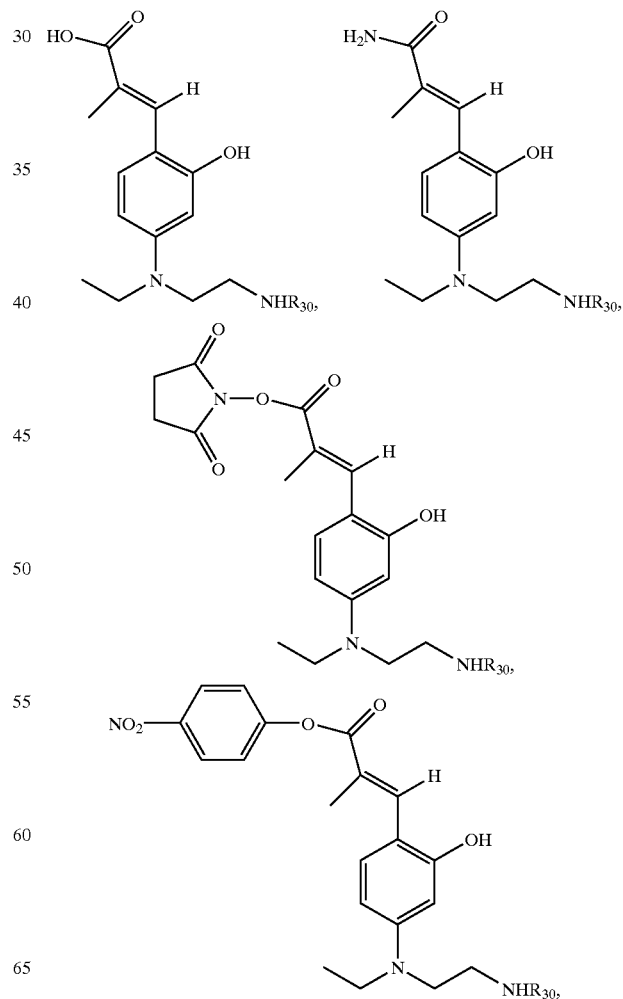

-continued
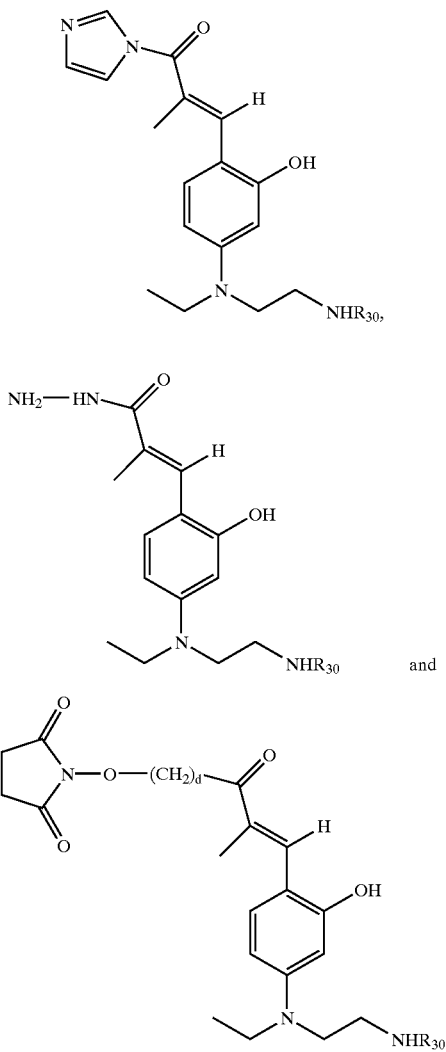
wherein d is a positive integer and $R_{30}$ is H, tBoc, fMoc or a blocking group.
17. A compound of claim 1, selected from the group consisting of:
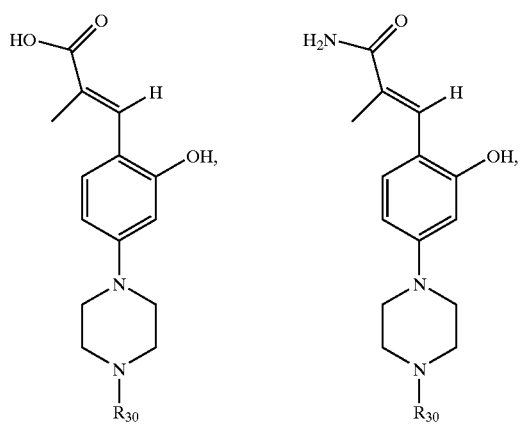
-continued
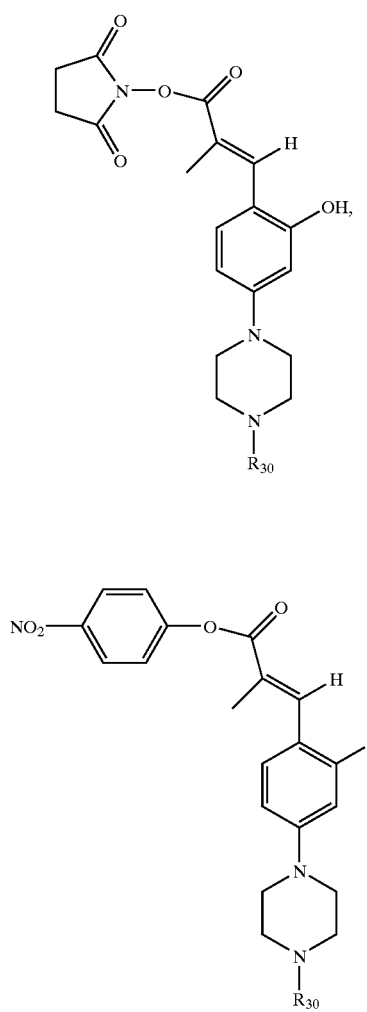
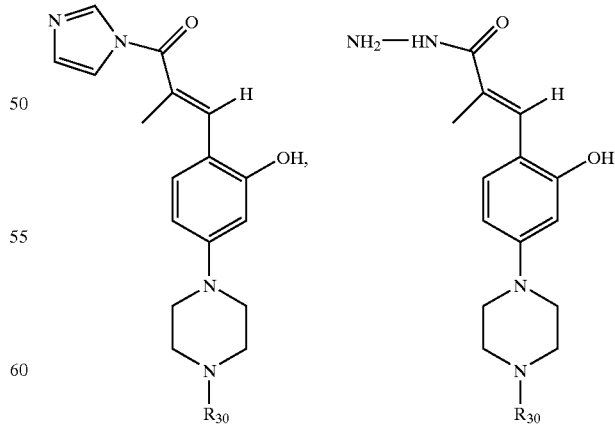
and -continued
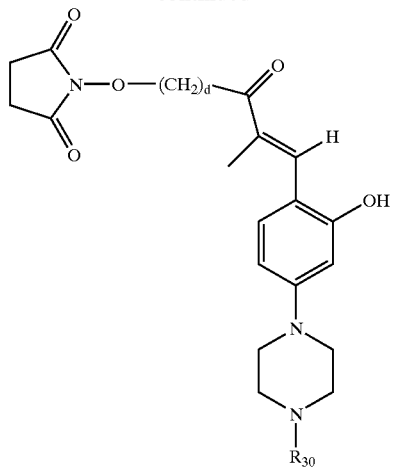
wherein d is a positive integer and $R_{30}$ is H, tBoc, fMoc or a blocking group.
18. A compound of claim 1, selected from the group consisting of:
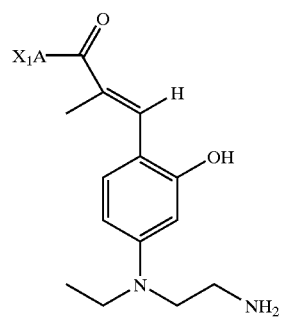 and 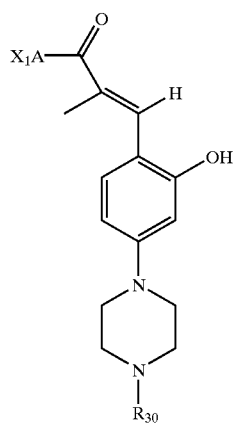
wherein $X_1A$ is a residue of a releasable biologically active moiety; and $R_{30}$ is H, tBoc, fMoc or a blocking group.
19. A compound of claim 1, selected from the group consisting of:
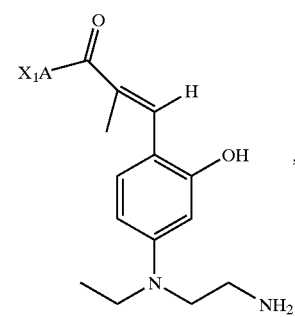, 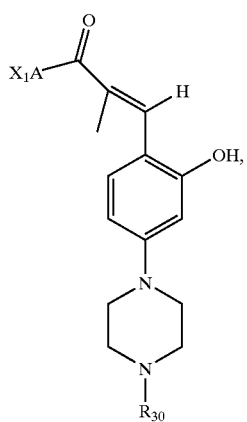,
-continued
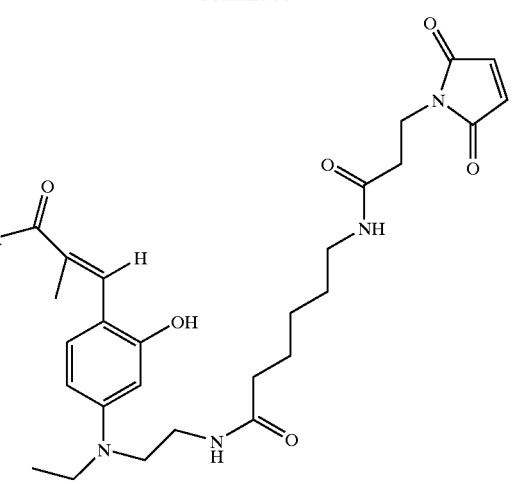
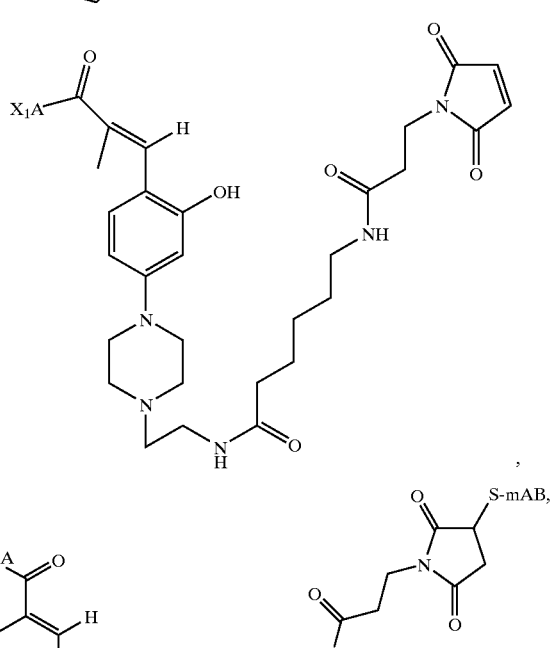
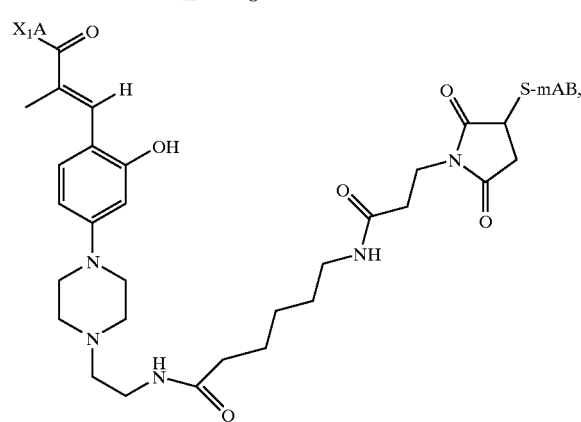

-continued
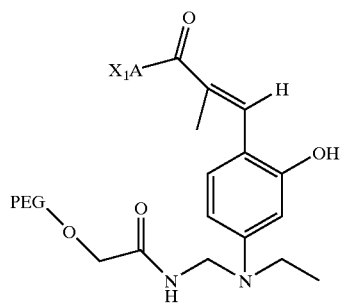
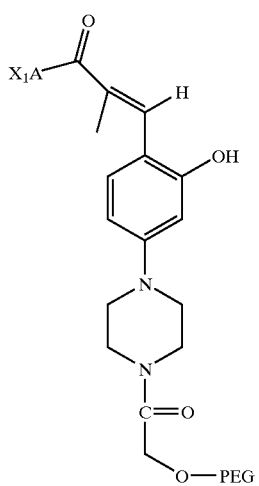
wherein $X_1A$ is a residue of a releasable biologically active moiety; and $R_{30}$ is H, tBoc, fMoc or a blocking group.
20. A compound of claim 19, selected from the group consisting of:
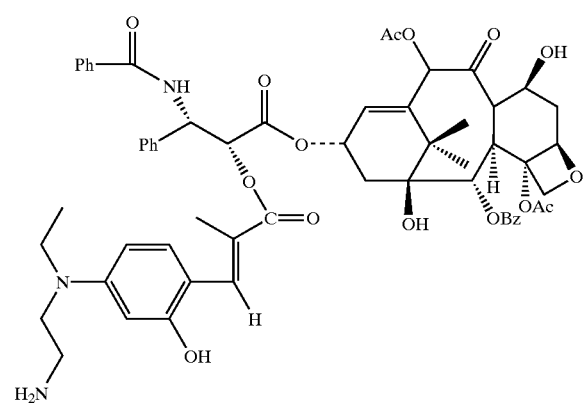
and
-continued
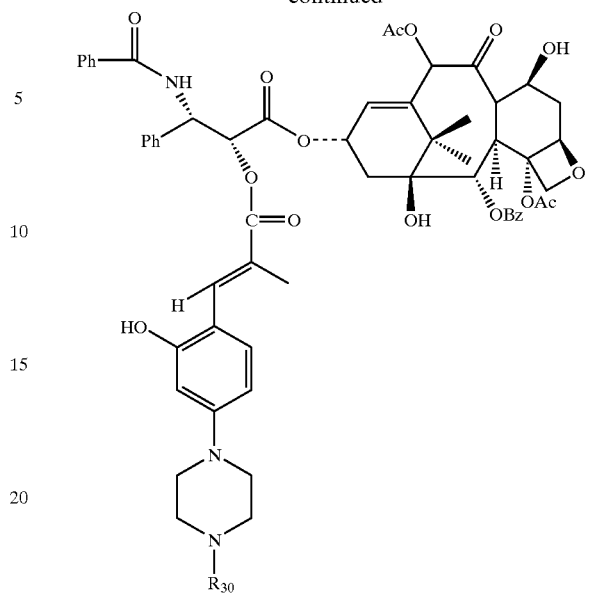
wherein $R_{30}$ is H, tBoc, fMoc or a blocking group.
21. A compound of claim 19, wherein $X_1A$ is selected from the group consisting of:
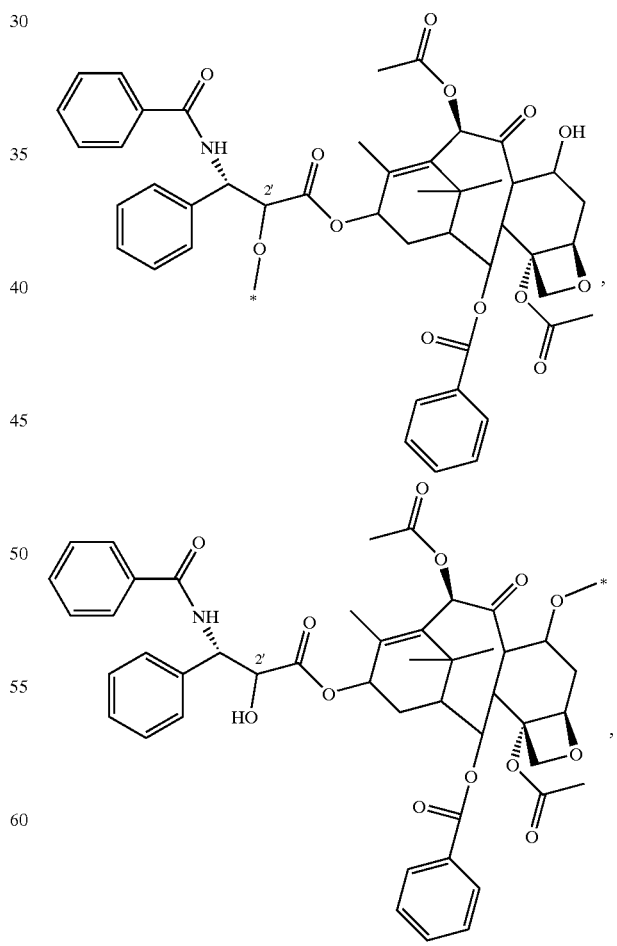

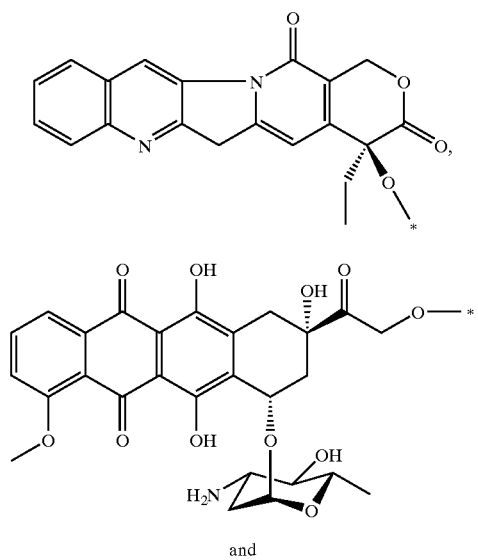
and
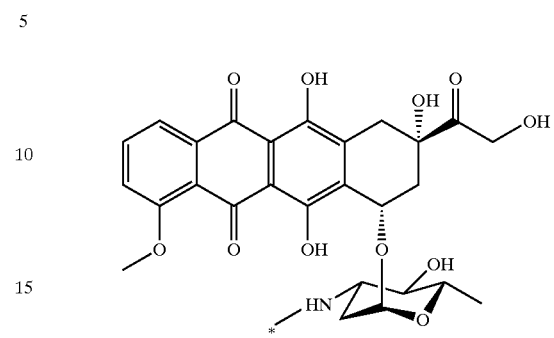
where * represents the point of attachment.
22. A compound of claim 19, selected from the group consisting of
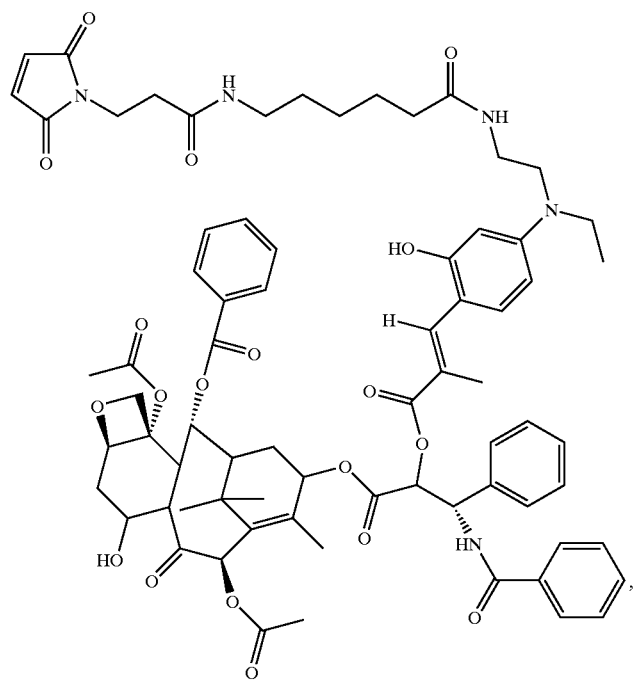

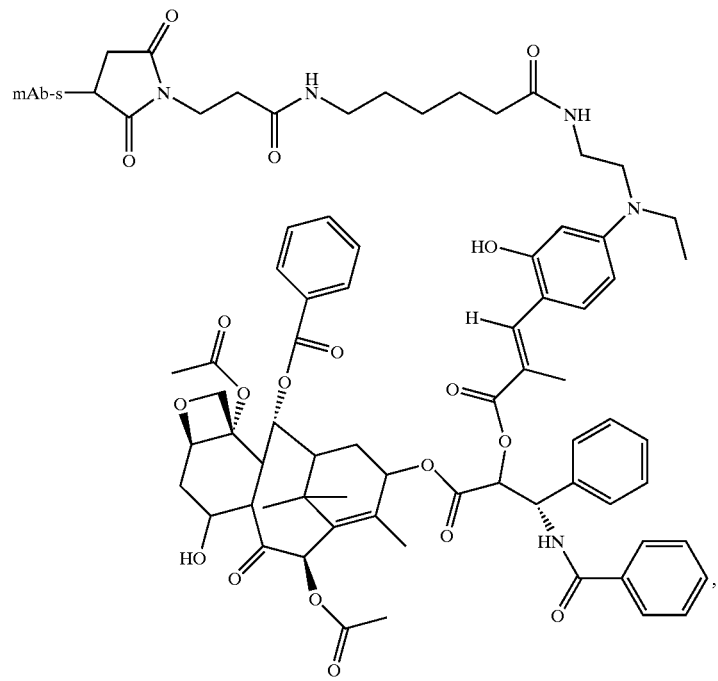
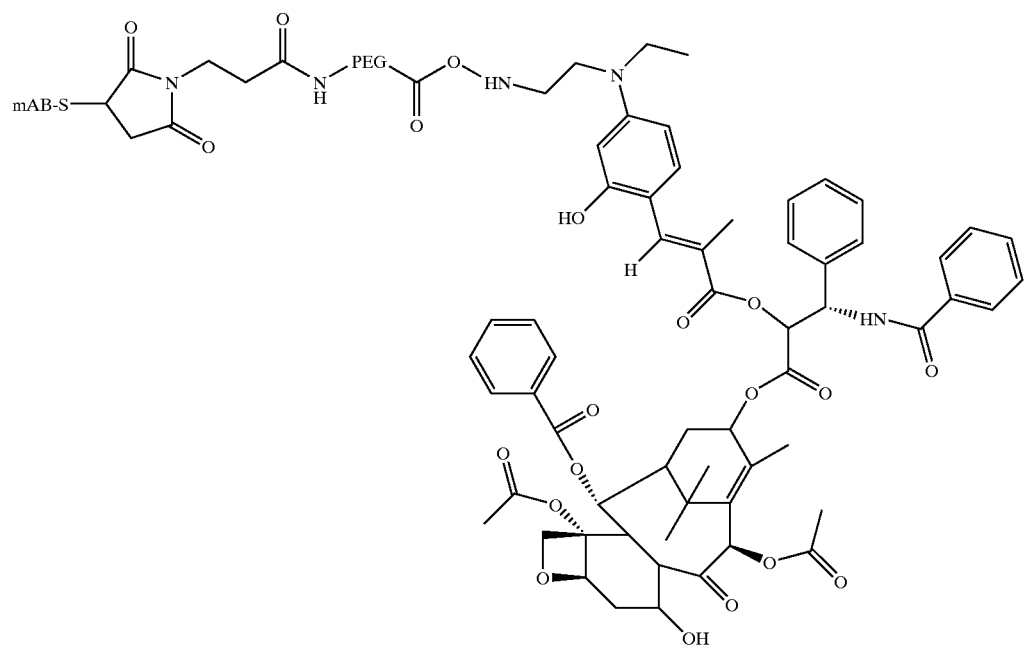

-continued

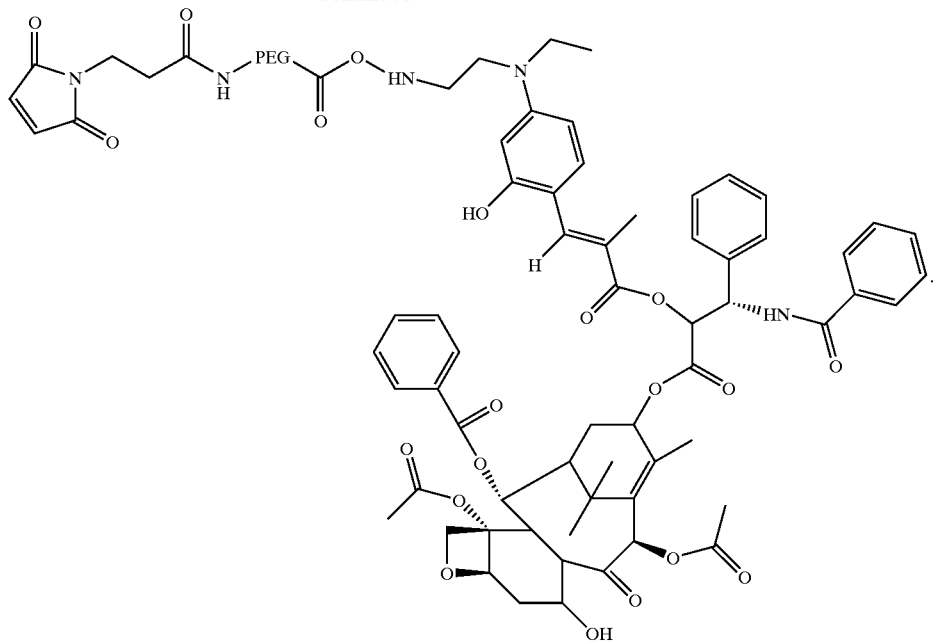

23. The compound of claim 1, wherein S is O, $R_2$ is H, $R_7$ is $CH_3CH_2$; $R_8$ is $-(CR_9R_{10})_n-NR_{22}-R_{11}$, n is 2, and $R_9$ and $R_{10}$ are both H.

24. The compound of claim 1, wherein $R_1$, $R_2$, $R_3$, $R_4$, $R_5$, and $R_6$ are independently selected from the group consisting of H, $CH_3$ and $CH_3CH_2$.

25. The compound of claim 1, wherein $R_7$ is $CH_3CH_2$; wherein $R_8$ is $-(CR_9R_{10})_n-NR_{22}-R_{11}$, n is 2, and $R_9$ and $R_{10}$ are both H.

26. A pharmaceutically acceptable salt of the compound of claim 1.

27. A pharmaceutically acceptable salt of the compound of claim 20.

28. A pharmaceutically acceptable salt of the compound of claim 21.

29. A method of treating mammals with prodrugs, comprising:
administering to a mammal in need of such treatment an effective amount of a prodrug compound of claim 1, where $X_1A$ is a residue of a releasable biologically active moiety, and allowing the releasable biologically active moiety to release from the prodrug in vivo.

30. The method of claim 29, further comprising exposing the prodrug compound of claim 1 to an energy source after administration to said mammal.

31. The method of claim 30, where n the energy source is white light having a wavelength in the range from 340 to 700 nm.

32. The method of claim 31, wherein the energy source is white light having a wavelength in the range from 350–420 nm.

33. The method of claim 30, wherein the energy source is selected from the group consisting of microwave, ultrasound, radio energy, gamma radiation, radioactivity, ultraviolet light and infrared light.

34. A method of preparing a conjugate, comprising:
reacting a cinnamic acid derivative of the formula

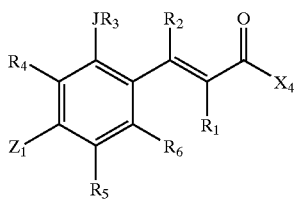

wherein
$X_4$ is a reactive terminal group;
$R_1$ and $R_2$ are individually selected from the group consisting of H, $CH_3$, $C_2-C_{10}$ alkyls, $C_2-C_{10}$ alkenyls or $C_2-C_{10}$ alkynyls, each of which can be substituted or unsubstituted; straight or branched, $C_2-C_{10}$ heteroalkyls, $C_2-C_{10}$ heteroalkenyls or $C_2-C_{10}$ heteroalkynyls and $-(CR_{15}R_{16})_p-D$
wherein: $R_{15}$ and $R_{16}$ are individually selected from the group consisting of H, $CH_3$, $C_2-C_{10}$ alkyls, $C_2-C_{10}$ alkenyls or $C_2-C_{10}$ alkynyls, each of which can be substituted or unsubstituted; straight or branched; and $C_2-C_{10}$ heteroalkyls, $C_2-C_{10}$ heteroalkenyls or $C_2-C_{10}$ heteroalkynyls;
p is a positive integer from 1 to about 12;
D is selected from among $-SH$, $-OH$, $X_2$, $-CN$, $-OR_{19}$, $NHR_{20}$,

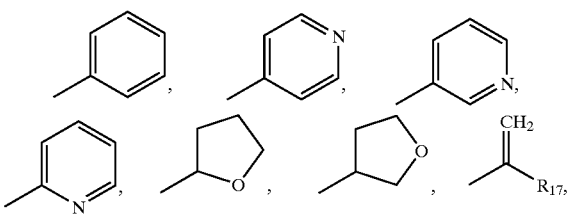

-continued

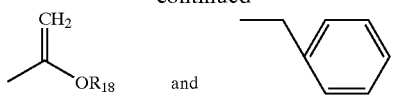
and wherein:
 $R_{17}$ is H, a $CH_3$ or $X_3$;
 $R_{18}$ is H, a $C_1$–$C_4$ alkyl or benzyl;
 $R_{19}$ is H, a $C_{1-4}$ alkyl, $X_2$ or benzyl;
 $R_{20}$ is H, a $C_{1-10}$ alkyl or —C(Ci)$R_{21}$,
  wherein $R_{21}$ is H, a $C_{1-4}$ alkyl or alkoxy, t-butoxy or benzyloxy;
 $X_2$ and $X_3$ are independently selected halogens;
$R_3$ is H, $CH_3$, or —C(O)(CR$_{15}$R$_{16}$)$_w$D,
 where w is 0 or an integer from 1 to about 12, and D is H or as described for $R_1$ and $R_2$
J is O, NH or S;
$R_4$, $R_5$, and $R_6$ are independently selected from the group consisting of H, $CH_3$, $C_2$–$C_{10}$ alkyls, $C_2$–$C_{10}$ alkenyls or $C_2$–$C_{10}$ alkynyls, each of which can be substituted or unsubstituted; straight or branched; $C_2$–$C_{10}$ heteroalkyls, heteroalkenyls or heteroalkynyls and halogens;
$Z_1$ is a member of the group consisting of

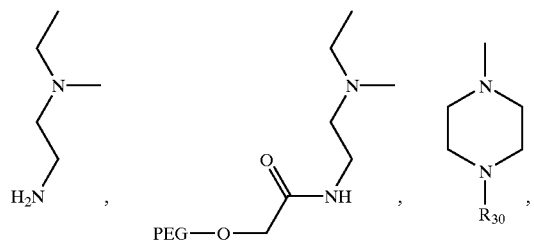

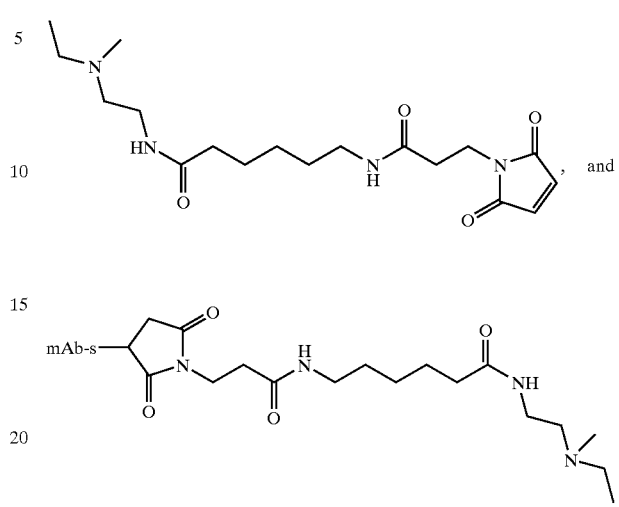

wherein
 $R_{30}$ is H, tBoc, fMoc or a blocking group;

with a biologically active moiety under conditions sufficient to cause covalent attachment of said biologically active moiety to said cinnamic acid derivative.

* * * * *